(12) United States Patent
Cabezon Silva et al.

(10) Patent No.: US 8,044,183 B2
(45) Date of Patent: Oct. 25, 2011

(54) PROCESS FOR THE PRODUCTION OF IMMUNOGENIC COMPOSITIONS

(75) Inventors: Teresa Cabezon Silva, Lenkebeek (BE); Joseph Cohen, Brussels (BE); Moncef Mohamed Slaoui, Rixensart (BE); Carlota Vinals Bassols, Liege (BE)

(73) Assignee: GlaxoSmithKline Biologicals S.A., Rixensart (BE)

(*) Notice: Subject to any disclaimer, the term of this patent is extended or adjusted under 35 U.S.C. 154(b) by 0 days.

(21) Appl. No.: 12/722,691

(22) Filed: Mar. 12, 2010

(65) Prior Publication Data

US 2010/0204458 A1    Aug. 12, 2010

Related U.S. Application Data

(63) Continuation of application No. 09/601,565, filed as application No. PCT/EP99/00660 on Feb. 2, 1999, now abandoned.

(30) Foreign Application Priority Data

Feb. 5, 1998  (GB) .................................. 9802543.0
Feb. 6, 1998  (GB) .................................. 9802650.3

(51) Int. Cl.
*C07K 1/113* (2006.01)
*C07K 1/06* (2006.01)
*C07K 1/16* (2006.01)
*A61K 39/00* (2006.01)

(52) U.S. Cl. ......... 530/403; 530/405; 530/406; 530/412

(58) Field of Classification Search .................. None
See application file for complete search history.

(56) References Cited

U.S. PATENT DOCUMENTS

| | | | |
|---|---|---|---|
| 4,302,386 A | 11/1981 | Stevens | |
| 4,384,995 A | 5/1983 | Stevens | |
| 4,526,716 A | 7/1985 | Stevens | |
| 5,500,354 A * | 3/1996 | Kitamura et al. | 435/69.4 |
| 5,593,876 A * | 1/1997 | Stamler et al. | 435/188 |
| 5,888,517 A | 3/1999 | Forsgren | |
| 5,905,142 A | 5/1999 | Murray | |
| 5,922,846 A | 7/1999 | Cerletti | |
| 5,925,729 A | 7/1999 | Boon et al. | |
| 5,942,235 A | 8/1999 | Paoletti | |
| 6,030,780 A | 2/2000 | Vinkemeier et al. | |
| 6,139,846 A | 10/2000 | Forsgren | |
| 6,287,569 B1 | 9/2001 | Kipps et al. | |
| 6,291,430 B1 | 9/2001 | Chaux | |
| 6,340,461 B1 | 1/2002 | Terman | |
| 6,426,217 B1 | 7/2002 | Chaux | |
| 6,475,783 B1 | 11/2002 | Lucas et al. | |
| 6,680,191 B1 | 1/2004 | Lucas et al. | |
| 6,686,147 B1 | 2/2004 | Scanlan et al. | |
| 6,716,809 B1 | 4/2004 | Schultz et al. | |
| 6,780,407 B1 | 8/2004 | Paoletti et al. | |
| 6,982,316 B1 | 1/2006 | Scanlan et al. | |
| 7,157,089 B1 | 1/2007 | Mizzen et al. | |
| 2002/0176865 A1 | 11/2002 | Lucas et al. | |
| 2003/0170256 A1 | 9/2003 | Lucas et al. | |

FOREIGN PATENT DOCUMENTS

| | | |
|---|---|---|
| EP | 0176493 | 4/1986 |
| WO | WO84/03443 | 9/1984 |
| WO | 365278 | 4/1990 |
| WO | WO91/18926 | 12/1991 |
| WO | WO92/20356 | 11/1992 |
| WO | WO94/00575 | 1/1994 |
| WO | 9405304 | 3/1994 |
| WO | WO 94/05304 | 3/1994 |
| WO | WO94/05304 | 3/1994 |
| WO | WO94/16716 | 8/1994 |
| WO | WO94/23031 | 10/1994 |
| WO | WO95/04542 | 2/1995 |
| WO | WO95/17210 | 6/1995 |
| WO | WO95/20974 | 8/1995 |
| WO | WO95/23874 | 9/1995 |
| WO | WO 96/10413 | 4/1996 |
| WO | WO96/22373 | 7/1996 |
| WO | WO96/10413 | 12/1996 |
| WO | WO97/01574 | 1/1997 |
| WO | WO97/13858 | 4/1997 |
| WO | WO97/46710 | 12/1997 |
| WO | WO98/10780 | 3/1998 |
| WO | WO98/14463 | 4/1998 |
| WO | WO98/20165 | 5/1998 |
| WO | WO98/49184 | 11/1998 |
| WO | WO99/14326 | 3/1999 |
| WO | WO99/40188 | 8/1999 |
| WO | WO99/53095 | 10/1999 |

OTHER PUBLICATIONS

Chen et al., Identification of the *MAGE-1* gene product by monoclonal and polyclonal antibodies, Proc. Natl. Acad. Sci. USA 91:1004-1008 (1994).
Okamoto et al., Induction of antibody response to human tumor antigens by gene therapy using a fusigenic viral liposome vaccine, Gene Therapy 4:969-976 (1997).
Shaw et al., Immunologic Studies on the Influenza A Virus Nonstructural Protein NS, Journal of Experimental Medicine 156:243-254 (1982).
European Search Report for 05076599.9 dated Oct. 20, 2005.
Hoon et al., Melanoma Patients Immunized with Melanoma Cell Vaccine Induce Antibody Responses to Recombinant MAGE-1 Antigen, The Journalof Immunology 154(2):730-737 (Jan. 1995).
Janson et al., Protein D, an Immunoglobulin D-Binding Protein of Haemophilus influenzae: Cloning, Nucleotide Sequence, and Expression in *Escherichia coli*, Infection and Immunity, 59(1), 119-125 (1991).
Traversari et al., IFN-y gene transfer restores HLA-class I expression and MAGE-3 antigen presentation to CTL in HLA-deficient small cell lung cancer, Gene Therapy, 4:1029-2035 (1997).

(Continued)

*Primary Examiner* — Karen Canella
(74) *Attorney, Agent, or Firm* — Eric J. Kron

(57) ABSTRACT

The present invention relates to a process for producing immunogenic polypeptides, comprising reducing disulfide bonds and blocking the resulting free thiol group with a blocking agent. The immunogenic peptides comprise a fragment of MAGE A3.

12 Claims, 19 Drawing Sheets

OTHER PUBLICATIONS

Gaugler, Human Gene MAGE-3 Codes for an Antigen Recognized on a Melanoma by Autologous Cytolytic T Lymphocytes, J. Exp. Med. 179:921-930 (1994).
Garcia et al., Nucleotide sequence and expression of the pneumococcal autolysin gene from its own promoter in *Escherichia coli*, Gene, 43:265-272 (1986).
Houen et al., Conjugation to preactivated proteins using divinylsufone and iodoacetic acid, Journal of Immunological Methods, 181:187-200 (1995).
Valmori et al., Analysis of MAGE-3-specific Cytolytic T Lymphocytes in Human Leukocyte Antigen-A2 Melanoma Patients, Cancer Research 57:735-741 (1997).
GenBank Accession No. NP_005353.
Carrell et al., Int. J. Cancer, 1996, vol. 67, pp. 417-422.
Kocher et al., Cancer Research, Jun. 1, 1995, vol. 55, pp. 2236-2239.
Maeurer et al., Melanoma Research 1996, vol. 6, pp. 11-24.
Marchand et al, "Immunisation of metastatic cancer patients with MAGE-3 protein combined with adjuvant SBAS-2: a clinical Report," European Journal of Cancer (2003) 39:70-77.
Vantomme, et al., Immunologic Analysis of a Phase I/II Study of Vaccination with MAGE-3 Protein Combined with the ASO2B Adjuvant in Patients with MAGE-3 Positive Tumors, J Immunother (Mar./Apr. 2004)27(2):124-135.
Imai, et al., "Sequence Analysis of the MAGE Gene Family Encoding Human Tumor-Rejection Antigens," Gene (1995) 160:287-290.
De Plaen et al., Structure Chromosomal Localization and Expression of 12 Genes of the MAGE Family, Immunogenetics (1994) 40:360-369.
Blake et al., International Journal of Peptide and Protein Research, 1992,vol. 40, pp. 62-65 Abtract only.
Reynolds et al. (International Journal of Cancer, 1997, vol. 72, pp. 972-976).
Vidard et al., (Journal of Immunology, 1992, vol. 149, pp. 498-504.
Sato et al., (Clinical Immunology and Immunopathology, 1997, vol. 5, pp. 265-272.
Berd, Proceed Amer Assoc Cancer Research, 1995, vol. 36, pp. 677-678.
Lauritzsen et al. (International Journal of Cancer, 1998, vol. 78, pp. 216-222).
Sarma et al., (Journal of Experimental Medicine, 1999, vol. 189, pp. 811-820.
Ohlen et al., (Journal of Immunology, 2001, vol. 166, pp. 2863-2870).
Antoinia et al. (International Immunology, 1995, vol. 7, pp. 715-725).
Algarra et al (International Journal of Clinical and Laboratory Research, 1997(27): 95-102 (Abstract).
Parmiani et al. (in: Heterogeneity of Cancer Cells, 1993, pp. 105-115.
Bodey et al. (Anticancer Research, Jul.-Aug. 2000, vol. 20, pp. 2665-2676.
Itoh et al., Journal of Biochemistry 1996, vol. 119, pp. 385-390 (Abstract).
Paul, Fundamental Immunology, (text), 1993, pp. 1163-1169.
Apostolopoulos et al (nature Medicine, 1998, vol. 4, pp. 315-320.
Jager et al (PNAS, 2000, vol. 97, pp. 12198-12203).
Semino et al (Journal of Biological Regulators and Homeostatic Agents, 1993, vol. 7 pp. 99-105) (Abstract).
Stedman's Medical Dictionary, 2000, definition of "vaccine".
Lee et al (Journal of Immunology, 1999, vol. 163 pp. 6292-6300.
Atanackovic et al, PNAS 2008, vol. 105, pp. 1650-1655.
Hofffman et al, International Journal of Cancer, 2005, vol. 115, pp. 98-104.
Van Der Bruggen, Science 254:1643-47 (1991).
Creighton, Trends in Biotechnology (TIBTech) 13:18-23 (1995).
Submission to European Patent Office in International Patent Application PCT/EP00660, dated Mar. 23, 2000, including Appendix 1 (13 pages).
PCT Written Opinion, PCT EP/99/00660, Nov. 26, 1999, 6 pp.
International Preliminary Examination Report, PCT EP/99/00660, 7 pp.
Reply to Communication PCT/IPEA/408, PCT EP/99/00660, Mar. 23, 2000, 3 pp.
Decision to Grant European Patent, EP1053325 (EP99907476), Nov. 24, 2005, 4 pp.
Reply to the Examining Division, EP1053325 (EP99907476), Jul. 23, 2003, 8 pp.
Communication from the Examining Division—Communication pursuant to Article 96(2) EPC, EP1053325, (EP99907476), Oct. 1, 2003, 3 pp.
Communication regarding transmission of the European Search Report, European Search Report and European Search Opinion, EP1659179 (app No. 06075363.9), Dec. 14, 2006, 9 pp total.
Communication from Examining Division, EP1659179 (app No. 06075363.9), Apr. 28, 2008, 4pp.
Reply to Communication from Examining Division, EP1659179 (app No. 06075363.9), Sep. 30, 2008, 2 pp.
Communication from Examining Division, EP1659179 (app No. 06075363.9), Nov. 27, 2009, 3 pp.
Reply to Communication from Examining Division, EP1659178 (app No. 06075362), Sep. 30, 2008, 3 pp.
Communication from Examining Division, EP1659178 (app No. 06075362), Apr. 28, 2008, 5 pp.
Brasseur et al., Letter to the editor, Int. J. Cancer 52 :839-841 (1992).
Brasseur et al., "Expression of MAGE genes in primary and metastatic cutaneous melanoma," Int. J. Cancer 63 :375-380 (1995).
Chen et al., "Identification of multiple cancer/testis antigens by allogeneic antibody screening of a melanoma cell line library," PNAS USA 95:6919-6923 (1998).
Van der Bruggen et al., "A gene encoding an antigen recognized by cytolytic T lymphocytes on a human melanoma," Science 254:1643-1647 (1991).
Van Pel and Boon, "Protection against a nonimmunogenic mouse leukemia by an immunogenic variant obtained by mutagenesis," PNAS USA 79:4718-4722 (1982).
Weynants et al., "Expression of mage genes by non-small-cell lung carcinomas," Int. J. Cancer 56 :826-829 (1994).
PCT EP/99/00660 PCT Written Opinion, Nov. 26, 1999 (6pp).
PCT EP/99/00660 International Preliminary Examination Report (7 pp).
PCT EP/99/006600 Reply to Communication PCT/IPEA/408 (PCT Chapter 2 procedure) Mar. 23, 2000 (3 pp).
EP1053325 (app. No. 99907476.8) Reply to the Examining Division, Jul. 23, 2003 (8 pp).
EP1053325 (app. No. 99907476.8) Communication from Exam Division, Jun. 17, 2003 (1 p).
EP1053325 (app. No. 99907476.8) Annex to the Communication from Exam Division, Jun. 17, 2003 (2 pp).
EP1053325 (app. No. 99907476.8) Communication from the Examining Division, Oct. 1, 2003 (1 p).
EP1053325 (app. No. 99907476.8) Annex to the Communication from the Examining Division, Oct. 1, 2003 (2 pp).
EP1584685, Reply to Communication from Exam Division, Sep. 9, 2008 (2pp).
EP1584685, Communication from Examining Division, May 7, 2008 (2pp).
EP1584685, Annex to the Communication from the Examining Division, May 7, 2008 (3pp).
EP1584685, Appendix 1, May 7, 2008 (8 pp).
EP1584685, EP Search Opinion, Oct. 20, 2005 (5pp).
EP1659179 (app No. 06075363.9) Communication regarding transmission of the European Search Report, Dec. 14, 2006 (1 p).
EP1659179 (app No. 06075363.9) European Search Report, Dec. 14, 2006 (3 pp).
EP1659179 (app No. 06075363.9) European Search Opinion, Dec. 14, 2006 (5 pp).
EP1659179 (app No. 06075363.9) Communication from the Examining Division, Apr. 28, 2008 (2 pp).
EP1659179 (app No. 06075363.9) Annex to the Communication from the Examining Division, Apr. 28, 2008 (2 pp).
EP1659179 (app No. 06075363.9) Reply to Communication from Examining Division, Sep. 30, 2008 (1 p).
EP1659179 (app No. 06075363.9) Communication from Examining Division, Nov. 27, 2009 (1 p).
EP1659179 (app No. 06075363.9) Annex to the Communication from the Examining Division, Nov. 27, 2009 (2 pp).
EP 1659178 (app No. 06075362) European Search Opinion, Dec. 15, 2006 (5pp).
EP 1659178 (app No. 06075362) European Search Report, Dec. 15, 2006 (3pp).

* cited by examiner

LPD-MAGE-3-His construction of the expression vector pRIT 14586 construction of plasmid pRIT 14477 expressing the fusion protein Prot.D 1/3-Mage 3-His tail.

Western blot analysis of LPD-MAGE-3-His protein
Anti-MAGE-3 monoclonal antibodies Mab 32 and Mab 54

Anti-Mage3 antibodies in the serum of mice
immunized with LipoD Mage3 His in SBAS2 or not Anti-Mage3 antibodies in the serum of mice
immunized with LipoD Mage3 His in SBAS2 or not

| Subclass-specific antibody responses in Balb/c mice | | | | | | |
|---|---|---|---|---|---|---|
| | Tot. IgG | IgG1 | IgG2a | IgG2b | IgA | IgM |
| PBS | 0 | 0 | 0 | 0 | 0 | 0 |
| SBAS2 | 733 | 719 | 378 | 11 | 0 | 0 |
| LPD Mg3 His | 6182 | 2049 | 2058 | 1835 | 0 | 0 |
| LPD Mg3 H /SBAS2 | 44321 | 267884 | 31325 | 12160 | 0 | 0 |

| | Tot. IgG | IgG1 | IgG2a | IgG2b | IgA | IgM |
|---|---|---|---|---|---|---|
| PBS | 807 | 405 | 718 | 22.8 | 2.8 | 33.8 |
| SBAS2 | 37 | 137 | 0 | 0 | 0 | 19 |
| LPD Mg3 His | 5471 | 1343 | 332 | 4540 | 135 | 5 |
| LPD Mg3 H /SBAS2 | 11489 | 2477 | 2070 | 8118 | 55 | 46 |

Subclass-specific antibody responses in C57BL/6 mice

Construction of plasmid pRIT14426

Plasmid map of pRIT14426 construction of plasmid pRIT 14613 construction of plasmid pRIT 14614

Construction of plasmid pRIT 14646

SEQUENCE LISTING

```
<160> NUMBER OF SEQ ID NOS: 16

<210> SEQ ID NO 1
<211> LENGTH: 1353
<212> TYPE: DNA
<213> ORGANISM: Artificial
<220> FEATURE:
<223> OTHER INFORMATION: DNA encoding fusion protein of Lipoprotein D
      fragment, Mage3 fragment, and histidine tail
<220> FEATURE:
<221> NAME/KEY: CDS
<222> LOCATION: (1)..(1350)

<400> SEQUENCE: 1 atg gat cca aaa act tta gcc ctt tct tta tta gca gct ggc gta cta      48
Met Asp Pro Lys Thr Leu Ala Leu Ser Leu Leu Ala Ala Gly Val Leu
1               5                   10                  15 gca ggt tgt agc agc cat tca tca aat atg gcg aat acc caa atg aaa      96
Ala Gly Cys Ser Ser His Ser Ser Asn Met Ala Asn Thr Gln Met Lys
            20                  25                  30 tca gac aaa atc att att gct cac cgt ggt gct agc ggt tat tta cca     144
Ser Asp Lys Ile Ile Ile Ala His Arg Gly Ala Ser Gly Tyr Leu Pro
        35                  40                  45 gag cat acg tta gaa tct aaa gca ctt gcg ttt gca caa cag gct gat     192
Glu His Thr Leu Glu Ser Lys Ala Leu Ala Phe Ala Gln Gln Ala Asp
    50                  55                  60 tat tta gag caa gat tta gca atg act aag gat ggt cgt tta gtg gtt     240
Tyr Leu Glu Gln Asp Leu Ala Met Thr Lys Asp Gly Arg Leu Val Val
65                  70                  75                  80 att cac gat cac ttt tta gat ggc ttg act gat gtt gcg aaa aaa ttc     288
Ile His Asp His Phe Leu Asp Gly Leu Thr Asp Val Ala Lys Lys Phe
                85                  90                  95
```

-continued

| | | |
|---|---|---|
| cca cat cgt cat cgt aaa gat ggc cgt tac tat gtc atc gac ttt acc<br>Pro His Arg His Arg Lys Asp Gly Arg Tyr Tyr Val Ile Asp Phe Thr<br>100              105              110 | 336 | |
| tta aaa gaa att caa agt tta gaa atg aca gaa aac ttt gaa acc atg<br>Leu Lys Glu Ile Gln Ser Leu Glu Met Thr Glu Asn Phe Glu Thr Met<br>115              120              125 | 384 | |
| gat ctg gaa cag cgt agt cag cac tgc aag cct gaa gaa ggc ctt gag<br>Asp Leu Glu Gln Arg Ser Gln His Cys Lys Pro Glu Glu Gly Leu Glu<br>130              135              140 | 432 | |
| gcc cga gga gag gcc ctg ggc ctg gtg ggt gcg cag gct cct gct act<br>Ala Arg Gly Glu Ala Leu Gly Leu Val Gly Ala Gln Ala Pro Ala Thr<br>145              150              155              160 | 480 | |
| gag gag cag gag gct gcc tcc tcc tct tct act cta gtt gaa gtc acc<br>Glu Glu Gln Glu Ala Ala Ser Ser Ser Ser Thr Leu Val Glu Val Thr<br>              165              170              175 | 528 | |
| ctg ggg gag gtg cct gct gcc gag tca cca gat cct ccc cag agt cct<br>Leu Gly Glu Val Pro Ala Ala Glu Ser Pro Asp Pro Pro Gln Ser Pro<br>              180              185              190 | 576 | |
| cag gga gcc tcc agc ctc ccc act acc atg aac tac cct ctc tgg agc<br>Gln Gly Ala Ser Ser Leu Pro Thr Thr Met Asn Tyr Pro Leu Trp Ser<br>              195              200              205 | 624 | |
| caa tcc tat gag gac tcc agc aac caa gaa gag gag ggg cca agc acc<br>Gln Ser Tyr Glu Asp Ser Ser Asn Gln Glu Glu Glu Gly Pro Ser Thr<br>210              215              220 | 672 | |
| ttc cct gac ctg gag tcc gag ttc caa gca gca ctc agt agg aag gtg<br>Phe Pro Asp Leu Glu Ser Glu Phe Gln Ala Ala Leu Ser Arg Lys Val<br>225              230              235              240 | 720 | |
| gcc gaa ttg gtt cat ttt ctg ctc ctc aag tat cga gcc agg gag ccg<br>Ala Glu Leu Val His Phe Leu Leu Leu Lys Tyr Arg Ala Arg Glu Pro<br>              245              250              255 | 768 | |
| gtc aca aag gca gaa atg ctg ggg agt gtc gtc gga aat tgg cag tat<br>Val Thr Lys Ala Glu Met Leu Gly Ser Val Val Gly Asn Trp Gln Tyr<br>              260              265              270 | 816 | |
| ttc ttt cct gtg atc ttc agc aaa gct tcc agt tcc ttg cag ctg gtc<br>Phe Phe Pro Val Ile Phe Ser Lys Ala Ser Ser Ser Leu Gln Leu Val<br>              275              280              285 | 864 | |
| ttt ggc atc gag ctg atg gaa gtg gac ccc atc ggc cac ttg tac atc<br>Phe Gly Ile Glu Leu Met Glu Val Asp Pro Ile Gly His Leu Tyr Ile<br>290              295              300 | 912 | |
| ttt gcc acc tgc ctg ggc ctc tcc tac gat ggc ctg ctg ggt gac aat<br>Phe Ala Thr Cys Leu Gly Leu Ser Tyr Asp Gly Leu Leu Gly Asp Asn<br>305              310              315              320 | 960 | |
| cag atc atg ccc aag gca ggc ctc ctg ata atc gtc ctg gcc ata atc<br>Gln Ile Met Pro Lys Ala Gly Leu Leu Ile Ile Val Leu Ala Ile Ile<br>              325              330              335 | 1008 | |
| gca aga gag ggc gac tgt gcc cct gag gag aaa atc tgg gag gag ctg<br>Ala Arg Glu Gly Asp Cys Ala Pro Glu Glu Lys Ile Trp Glu Glu Leu<br>              340              345              350 | 1056 | |
| agt gtg tta gag gtg ttt gag ggg agg gaa gac agt atc ttg ggg gat<br>Ser Val Leu Glu Val Phe Glu Gly Arg Glu Asp Ser Ile Leu Gly Asp<br>              355              360              365 | 1104 | |
| ccc aag aag ctg ctc acc caa cat ttc gtg cag gaa aac tac ctg gag<br>Pro Lys Lys Leu Leu Thr Gln His Phe Val Gln Glu Asn Tyr Leu Glu<br>370              375              380 | 1152 | |
| tac cgg cag gtc ccc ggc agt gat cct gca tgt tat gaa ttc ctg tgg<br>Tyr Arg Gln Val Pro Gly Ser Asp Pro Ala Cys Tyr Glu Phe Leu Trp<br>385              390              395              400 | 1200 | |
| ggt cca agg gcc ctc gtt gaa acc agc tat gtg aaa gtc ctg cac cat<br>Gly Pro Arg Ala Leu Val Glu Thr Ser Tyr Val Lys Val Leu His His<br>              405              410              415 | 1248 | |

```
atg gta aag atc agt gga gga cct cac att tcc tac cca ccc ctg cat         1296
Met Val Lys Ile Ser Gly Gly Pro His Ile Ser Tyr Pro Pro Leu His
        420                 425                 430 gag tgg gtt ttg aga gag ggg gaa gag ggc ggt cat cac cat cac cat         1344
Glu Trp Val Leu Arg Glu Gly Glu Glu Gly Gly His His His His His
        435                 440                 445 cac cat taa                                                             1353
His His
    450

<210> SEQ ID NO 2
<211> LENGTH: 450
<212> TYPE: PRT
<213> ORGANISM: Artificial
<220> FEATURE:
<223> OTHER INFORMATION: Synthetic Construct

<400> SEQUENCE: 2

Met Asp Pro Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Met
        115                 120                 125

Asp Leu Glu Gln Arg Ser Gln His Cys Lys Pro Glu Glu Gly Leu Glu
    130                 135                 140

Ala Arg Gly Glu Ala Leu Gly Leu Val Gly Ala Gln Ala Pro Ala Thr
145                 150                 155                 160

Glu Glu Gln Glu Ala Ser Ser Ser Thr Leu Val Glu Val Thr
                165                 170                 175

Leu Gly Glu Val Pro Ala Ala Gly Ser Pro Asp Pro Gln Ser Pro
        180                 185                 190

Gln Gly Ala Ser Ser Leu Pro Thr Thr Met Asn Tyr Pro Leu Trp Ser
    195                 200                 205

Gln Ser Tyr Glu Asp Ser Ser Asn Gln Glu Glu Gly Pro Ser Thr
    210                 215                 220

Phe Pro Asp Leu Glu Ser Glu Phe Gln Ala Ala Leu Ser Arg Lys Val
225                 230                 235                 240

Ala Glu Leu Val His Phe Leu Leu Lys Tyr Arg Ala Arg Glu Pro
                245                 250                 255

Val Thr Lys Ala Glu Met Leu Gly Ser Val Val Gly Asn Trp Gln Tyr
            260                 265                 270

Phe Phe Pro Val Ile Phe Ser Lys Ala Ser Ser Leu Gln Leu Val
        275                 280                 285

Phe Gly Ile Glu Leu Met Glu Val Asp Pro Ile Gly His Leu Tyr Ile
    290                 295                 300
```

```
Phe Ala Thr Cys Leu Gly Leu Ser Tyr Asp Gly Leu Leu Gly Asp Asn
305                 310                 315                 320

Gln Ile Met Pro Lys Ala Gly Leu Leu Ile Val Leu Ala Ile Ile
            325                 330                 335

Ala Arg Glu Gly Asp Cys Ala Pro Glu Lys Ile Trp Glu Glu Leu
        340                 345                 350

Ser Val Leu Glu Val Phe Glu Gly Arg Glu Asp Ser Ile Leu Gly Asp
        355                 360                 365

Pro Lys Lys Leu Leu Thr Gln His Phe Val Gln Glu Asn Tyr Leu Glu
370                 375                 380

Tyr Arg Gln Val Pro Gly Ser Asp Pro Ala Cys Tyr Glu Phe Leu Trp
385                 390                 395                 400

Gly Pro Arg Ala Leu Val Glu Thr Ser Tyr Val Lys Val Leu His His
                405                 410                 415

Met Val Lys Ile Ser Gly Gly Pro His Ile Ser Tyr Pro Pro Leu His
                420                 425                 430

Glu Trp Val Leu Arg Glu Gly Glu Gly Gly His His His His
                435                 440                 445

His His
    450
```

<210> SEQ ID NO 3
<211> LENGTH: 1341
<212> TYPE: DNA
<213> ORGANISM: Artificial
<220> FEATURE:
<223> OTHER INFORMATION: DNA encoding fusion protein of Lipoprotein D
      fragment, MAGE1 fragment, and histidine tail.

<400> SEQUENCE: 3

```
atggatccaa aaactttagc cctttcttta ttagcagctg gcgtactagc aggttgtagc      60
agccattcat caaatatggc gaatacccaa atgaaatcag acaaaatcat tattgctcac    120
cgtggtgcta gcggttattt accagagcat acgttagaat ctaaagcact tgcgtttgca    180
caacaggctg attatttaga gcaagattta gcaatgacta aggatggtcg tttagtggtt    240
attcacgatc actttttaga tggcttgact gatgttgcga aaaaattccc acatcgtcat    300
cgtaaagatg gccgttacta tgtcatcgac tttaccttaa agaaattcaa agtttagaa     360
atgacagaaa acttttgaaac catgggctct ctggaacagc gtagtctgca ctgcaagcct    420
gaggaagccc ttgaggccca caagaggcc ctgggcctgg tgtgtgtgca ggctgccacc    480
tcctcctcct ctcctctggt cctgggcacc ctggaggagg tgcccactgc tgggtcaaca    540
gatcctcccc agagtcctca gggagcctcc gcctttccca ctaccatcaa cttcactcga    600
cagaggcaac ccagtgaggg ttccagcagc cgtgaagagg aggggccaag caccctcttgt    660
atcctggagt ccttgttccg agcagtaatc actaagaagg tggctgattt ggttggtttt    720
ctgctcctca aatatcgagc cagggagcca gtcacaaagg cagaaatgct ggagagtgtc    780
atcaaaaatt acaagcactg ttttcctgag atcttcggca aagcctctga gtccttgcag    840
ctggtctttg gcattgacgt gaaggaagca gaccccaccg ccactcctta tgtccttgtc    900
acctgcctag tctctcccta tgatggcctg ctgggtgata atcagatcat gcccaagaca    960
ggcttcctga taattgtcct ggtcatgatt gcaatggagg cggccatgc tcctgaggag    1020
gaaatctggg aggagctgag tgtgattgga gtgtatgatg ggagggagca cagtgcctat   1080
ggggagccca ggaagctgct cacccaagat ttggtgcagg aaaagtacct ggagtaccgg   1140
caggtgccgg acagtgatcc cgcacgctat gagttcctgt ggggtccaag ggccctcgct   1200
```

```
gaaaccagct atgtgaaagt ccttgagtat gtgatcaagg tcagtgcaag agttcgcttt    1260
ttcttcccat ccctgcgtga agcagctttg agagaggagg aagagggagt cggcggtcat    1320
caccatcacc atcaccatta a                                              1341
```

<210> SEQ ID NO 4
<211> LENGTH: 446
<212> TYPE: PRT
<213> ORGANISM: Artificial
<220> FEATURE:
<223> OTHER INFORMATION: Fusion protein of LPD-MAGE1-Histidine

<400> SEQUENCE: 4

```
Met Asp Pro Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Leu Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Met
        115                 120                 125

Gly Ser Leu Glu Gln Arg Ser Leu His Cys Lys Pro Glu Glu Ala Leu
    130                 135                 140

Glu Ala Gln Gln Glu Ala Leu Gly Leu Val Cys Val Gln Ala Ala Thr
145                 150                 155                 160

Ser Ser Ser Ser Pro Leu Val Leu Gly Thr Leu Glu Glu Val Pro Thr
                165                 170                 175

Ala Gly Ser Thr Asp Pro Pro Gln Ser Pro Gln Gly Ala Ser Ala Phe
            180                 185                 190

Pro Thr Thr Ile Asn Phe Thr Arg Gln Arg Gln Pro Ser Glu Gly Ser
        195                 200                 205

Ser Ser Arg Glu Glu Glu Gly Pro Ser Thr Ser Cys Ile Leu Glu Ser
    210                 215                 220

Leu Phe Arg Ala Val Ile Thr Lys Lys Val Ala Asp Leu Val Gly Phe
225                 230                 235                 240

Leu Leu Leu Lys Tyr Arg Ala Arg Glu Pro Val Thr Lys Ala Glu Met
                245                 250                 255

Leu Glu Ser Val Ile Lys Asn Tyr Lys His Cys Phe Pro Glu Ile Phe
            260                 265                 270

Gly Lys Ala Ser Glu Ser Leu Gln Leu Val Phe Gly Ile Asp Val Lys
        275                 280                 285

Glu Ala Asp Pro Thr Gly His Ser Tyr Val Leu Val Thr Cys Leu Gly
    290                 295                 300

Leu Ser Tyr Asp Gly Leu Leu Gly Asp Asn Gln Ile Met Pro Lys Thr
305                 310                 315                 320

Gly Phe Leu Ile Ile Val Leu Val Met Ile Ala Met Glu Gly Gly His
                325                 330                 335
```

```
Ala Pro Glu Glu Glu Ile Trp Glu Glu Leu Ser Val Met Glu Val Tyr
            340                 345                 350

Asp Gly Arg Glu His Ser Ala Tyr Gly Glu Pro Arg Lys Leu Leu Thr
            355                 360                 365

Gln Asp Leu Val Gln Lys Tyr Leu Glu Tyr Arg Gln Val Pro Asp
            370                 375                 380

Ser Asp Pro Ala Arg Tyr Glu Phe Leu Trp Gly Pro Arg Ala Leu Ala
385                 390                 395                 400

Glu Thr Ser Tyr Val Lys Val Leu Glu Tyr Val Ile Lys Val Ser Ala
            405                 410                 415

Arg Val Arg Phe Phe Phe Pro Ser Leu Arg Glu Ala Ala Leu Arg Glu
            420                 425                 430

Glu Glu Glu Gly Val Gly Gly His His His His His His
            435                 440                 445

<210> SEQ ID NO 5
<211> LENGTH: 403
<212> TYPE: PRT
<213> ORGANISM: Artificial
<220> FEATURE:
<223> OTHER INFORMATION: Fusion protein of NS1-MAGE3, and Histidine tail

<400> SEQUENCE: 5

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
            35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Asp Leu Glu Gln Arg Ser Gln His Cys Lys Pro Glu Glu Gly Leu
                85                  90                  95

Glu Ala Arg Gly Glu Ala Leu Gly Leu Val Gly Ala Gln Ala Pro Ala
            100                 105                 110

Thr Glu Glu Gln Glu Ala Ala Ser Ser Ser Thr Leu Val Glu Val
            115                 120                 125

Thr Leu Gly Glu Val Pro Ala Ala Glu Ser Pro Asp Pro Pro Gln Ser
    130                 135                 140

Pro Gln Gly Ala Ser Ser Leu Pro Thr Thr Met Asn Tyr Pro Leu Trp
145                 150                 155                 160

Ser Gln Ser Tyr Glu Asp Ser Ser Asn Gln Glu Glu Glu Gly Pro Ser
                165                 170                 175

Thr Phe Pro Asp Leu Glu Ser Glu Phe Gln Ala Ala Leu Ser Arg Lys
            180                 185                 190

Val Ala Glu Leu Val His Phe Leu Leu Leu Lys Tyr Arg Ala Arg Glu
            195                 200                 205

Pro Val Thr Lys Ala Glu Met Leu Gly Ser Val Val Gly Asn Trp Gln
    210                 215                 220

Tyr Phe Phe Pro Val Ile Phe Ser Lys Ala Ser Ser Ser Leu Gln Leu
225                 230                 235                 240

Val Phe Gly Ile Glu Leu Met Glu Val Asp Pro Ile Gly His Leu Tyr
                245                 250                 255

Ile Phe Ala Thr Cys Leu Gly Leu Ser Tyr Asp Gly Leu Leu Gly Asp
```

```
                260                 265                 270
Asn Gln Ile Met Pro Lys Ala Gly Leu Leu Ile Ile Val Leu Ala Ile
            275                 280                 285

Ile Ala Arg Glu Gly Asp Cys Ala Pro Glu Glu Lys Ile Trp Glu Glu
        290                 295                 300

Leu Ser Val Leu Glu Val Phe Glu Gly Arg Glu Asp Ser Ile Leu Gly
305                 310                 315                 320

Asp Pro Lys Lys Leu Leu Thr Gln His Phe Val Gln Glu Asn Tyr Leu
                325                 330                 335

Glu Tyr Arg Gln Val Pro Gly Ser Asp Pro Ala Cys Tyr Glu Phe Leu
            340                 345                 350

Trp Gly Pro Arg Ala Leu Val Glu Thr Ser Tyr Val Lys Val Leu His
        355                 360                 365

His Met Val Lys Ile Ser Gly Gly Pro His Ile Ser Tyr Pro Pro Leu
    370                 375                 380

His Glu Trp Val Leu Arg Glu Gly Glu Glu Gly Gly His His His His
385                 390                 395                 400

His His His

<210> SEQ ID NO 6
<211> LENGTH: 1212
<212> TYPE: DNA
<213> ORGANISM: Artificial
<220> FEATURE:
<223> OTHER INFORMATION: DNA coding fusion protein NS1-MAGE3-His

<400> SEQUENCE: 6
atggatccaa acactgtgtc aagctttcag gtagattgct ttctttggca tgtccgcaaa      60
cgagttgcag accaagaact aggtgatgcc ccattccttg atcggcttcg ccagatcag     120 aaatccctaa aggaaggggg cagcactctt ggtctggaca tcgagacagc cacacgtgct     180
ggaaagcaga tagtggagcg gattctgaaa gaagaatccg atgaggcact aaaaatgacc     240
atggatctgg aacagcgtag tcagcactgc aagcctgaag aaggccttga ggcccgagga     300
gaggccctgg gcctggtggg tgcgcaggct cctgctactg aggagcagga ggctgcctcc     360
tcctcttcta ctctagttga agtcaccctg ggggaggtgc ctgctgccga gtcaccagat     420
cctccccaga gtcctcaggg agcctccagc tcccccacta ccatgaacta ccctctctgg     480
agccaatcct atgaggactc cagcaaccaa gaagaggagg ggccaagcac cttccctgac     540
ctggagtccg agttccaagc agcactcagt aggaaggtgg ccgaattggt tcattttctg     600
ctcctcaagt atcgagccag ggagccggtc acaaaggcag aaatgctggg gagtgtcgtc     660
ggaaattggc agtatttctt tcctgtgatc ttcagcaaag cttccagttc cttgcagctg     720
gtctttggca tcgagctgat ggaagtggac cccatcggcc acttgtacat ctttgccacc     780
tgcctgggcc tctcctacga tggcctgctg gtgacaatc agatcatgcc caaggcaggc     840
ctcctgataa tcgtcctggc cataatcgca agagagggcg actgtgcccc tgaggagaaa     900
atctgggagg agctgagtgt gttagaggtg tttgagggga gggaagacag tatcttgggg     960
gatcccaaga agctgctcac ccaacatttc gtgcaggaaa actacctgga gtaccggcag    1020
gtccccggca gtgatcctgc atgttatgaa ttcctgtggg gtccaagggc cctcgttgaa    1080
accagctatg tgaaagtcct gcaccatatg gtaaagatca gtggaggacc tcacatttcc    1140
tacccacccc tgcatgagtg ggttttgaga gaggggaag agggcggtca tcaccatcac    1200
catcaccatt aa                                                        1212
```

<210> SEQ ID NO 7
<211> LENGTH: 445
<212> TYPE: PRT
<213> ORGANISM: Artificial
<220> FEATURE:
<223> OTHER INFORMATION: Fusion protein of CLYTA-MAGE1-Histidine

<400> SEQUENCE: 7

Met Lys Gly Gly Ile Val His Ser Asp Gly Ser Tyr Pro Lys Asp Lys
1               5                   10                  15

Phe Glu Lys Ile Asn Gly Thr Trp Tyr Tyr Phe Asp Ser Ser Gly Tyr
            20                  25                  30

Met Leu Ala Asp Arg Trp Arg Lys His Thr Asp Gly Asn Trp Tyr Trp
        35                  40                  45

Phe Asp Asn Ser Gly Glu Met Ala Thr Gly Trp Lys Lys Ile Ala Asp
    50                  55                  60

Lys Trp Tyr Tyr Phe Asn Glu Glu Gly Ala Met Lys Thr Gly Trp Val
65                  70                  75                  80

Lys Tyr Lys Asp Thr Trp Tyr Tyr Leu Asp Ala Lys Glu Gly Ala Met
                85                  90                  95

Val Ser Asn Ala Phe Ile Gln Ser Ala Asp Gly Thr Gly Trp Tyr Tyr
            100                 105                 110

Leu Lys Pro Asp Gly Thr Leu Ala Asp Arg Pro Glu Leu Asp Met Gly
        115                 120                 125

Ser Leu Glu Gln Arg Ser Leu His Cys Lys Pro Glu Glu Ala Leu Glu
    130                 135                 140

Ala Gln Gln Glu Ala Leu Gly Leu Val Cys Val Gln Ala Ala Thr Ser
145                 150                 155                 160

Ser Ser Ser Pro Leu Val Leu Gly Thr Leu Glu Glu Val Pro Thr Ala
                165                 170                 175

Gly Ser Thr Asp Pro Pro Gln Ser Pro Gln Gly Ala Ser Ala Phe Pro
            180                 185                 190

Thr Thr Ile Asn Phe Thr Arg Gln Arg Gln Pro Ser Glu Gly Ser Ser
        195                 200                 205

Ser Arg Glu Glu Glu Gly Pro Ser Thr Ser Cys Ile Leu Glu Ser Leu
    210                 215                 220

Phe Arg Ala Val Ile Thr Lys Lys Val Ala Asp Leu Val Gly Phe Leu
225                 230                 235                 240

Leu Leu Lys Tyr Arg Ala Arg Glu Pro Val Thr Lys Ala Glu Met Leu
                245                 250                 255

Glu Ser Val Ile Lys Asn Tyr Lys His Cys Phe Pro Glu Ile Phe Gly
            260                 265                 270

Lys Ala Ser Glu Ser Leu Gln Leu Val Phe Gly Ile Asp Val Lys Glu
        275                 280                 285

Ala Asp Pro Thr Gly His Ser Tyr Val Leu Val Thr Cys Leu Gly Leu
    290                 295                 300

Ser Tyr Asp Gly Leu Leu Gly Asp Asn Gln Ile Met Pro Lys Thr Gly
305                 310                 315                 320

Phe Leu Ile Ile Val Leu Val Met Ile Ala Met Glu Gly Gly His Ala
                325                 330                 335

Pro Glu Glu Glu Ile Trp Glu Glu Leu Ser Val Met Glu Val Tyr Asp
            340                 345                 350

Gly Arg Glu His Ser Ala Tyr Gly Glu Pro Arg Lys Leu Leu Thr Gln
        355                 360                 365

Asp Leu Val Gln Glu Lys Tyr Leu Glu Tyr Arg Gln Val Pro Asp Ser

```
                 370                375                 380
Asp Pro Ala Arg Tyr Glu Phe Leu Trp Gly Pro Arg Ala Leu Ala Glu
385                 390                 395                 400

Thr Ser Tyr Val Lys Val Leu Glu Tyr Val Ile Lys Val Ser Ala Arg
                405                 410                 415

Val Arg Phe Phe Phe Pro Ser Leu Arg Glu Ala Ala Leu Arg Glu Glu
                420                 425                 430

Glu Glu Gly Val Gly Gly His His His His His His
                435                 440                 445
```

<210> SEQ ID NO 8
<211> LENGTH: 1338
<212> TYPE: DNA
<213> ORGANISM: Artificial
<220> FEATURE:
<223> OTHER INFORMATION: DNA coding fusion protein CLYTA-MAGE1-His

<400> SEQUENCE: 8

```
atgaaagggg gaattgtaca ttcagacggc tcttatccaa agacaagtt tgagaaaatc      60
aatggcactt gtactactt tgacagttca ggctatatgc ttgcagaccg ctggaggaag     120
cacacagacg gcaactggta ctggttcgac aactcaggcg aaatggctac aggctggaag    180
aaaatcgctg ataagtggta ctatttcaac gaagaaggtg ccatgaagac aggctgggtc    240
aagtacaagg acacttggta ctacttagac gctaaagaag gcgccatggt atcaaatgcc    300
tttatccagt cagcggacgg aacaggctgg tactacctca accagacgg aacactggca    360
gacaggccag aattggacat gggctctctg aacagcgta gtctgcactg caagcctgag    420
gaagcccttg aggcccaaca agaggccctg ggcctggtgt gtgtgcaggc tgccacctcc    480
tcctcctctc ctctggtcct gggcaccctg aggaggtgc ccactgctgg gtcaacagat    540
cctcccaga gtcctcaggg agcctccgcc tttcccacta ccatcaactt cactcgacag    600
aggcaaccca gtgagggttc cagcagccgt gaagaggagg ggccaagcac ctcttgtatc    660
ctggagtcct tgttccgagc agtaatcact aagaaggtgg ctgatttggt tggttttctg    720
ctcctcaaat atcgagccag ggagccagtc acaaaggcag aaatgctgga gagtgtcatc    780
aaaaattaca agcactgttt tcctgagatc ttcggcaaag cctctgagtc cttgcagctg    840
gtctttggca ttgacgtgaa ggaagcagac cccaccggcc actcctatgt ccttgtcacc    900
tgcctaggtc tctcctatga tggcctgctg ggtgataatc agatcatgcc aagacaggc    960
ttcctgataa ttgtcctggt catgattgca atggagggcg ccatgctcc tgaggaggaa   1020
atctgggagg agctgagtgt gatggaggtg tatgatggga gggagcacag tgcctatggg   1080
gagcccagga agctgctcac ccaagatttg gtgcaggaaa agtacctgga gtaccggcag   1140
gtgccggaca gtgatcccgc acgctatgag ttcctgtggg gtccaagggc cctcgctgaa   1200
accagctatg tgaaagtcct tgagtatgtg atcaaggtca gtgcaagagt cgctttttc   1260
ttcccatccc tgcgtgaagc agctttgaga gaggaggaag agggagtcgg cggtcatcac   1320
catcaccatc accattaa                                                 1338
```

<210> SEQ ID NO 9
<211> LENGTH: 453
<212> TYPE: PRT
<213> ORGANISM: Artificial
<220> FEATURE:
<223> OTHER INFORMATION: Fusion protein of CLYTA-MAGE3-Histidine

<400> SEQUENCE: 9

-continued

```
Met Lys Gly Gly Ile Val His Ser Asp Gly Ser Tyr Pro Lys Asp Lys
 1               5                  10                  15

Phe Glu Lys Ile Asn Gly Thr Trp Tyr Tyr Phe Asp Ser Ser Gly Tyr
             20                  25                  30

Met Leu Ala Asp Arg Trp Arg Lys His Thr Asp Gly Asn Trp Tyr Trp
         35                  40                  45

Phe Asp Asn Ser Gly Glu Met Ala Thr Gly Trp Lys Lys Ile Ala Asp
     50                  55                  60

Lys Trp Tyr Tyr Phe Asn Glu Glu Gly Ala Met Lys Thr Gly Trp Val
 65                  70                  75                  80

Lys Tyr Lys Asp Thr Trp Tyr Tyr Leu Asp Ala Lys Glu Gly Ala Met
             85                  90                  95

Val Ser Asn Ala Phe Ile Gln Ser Ala Asp Gly Thr Gly Trp Tyr Tyr
        100                 105                 110

Leu Lys Pro Asp Gly Thr Leu Ala Asp Arg Pro Glu Leu Ala Ser Met
        115                 120                 125

Leu Asp Met Asp Leu Glu Gln Arg Ser Gln His Cys Lys Pro Glu Glu
    130                 135                 140

Gly Leu Glu Ala Arg Gly Glu Ala Leu Gly Leu Val Gly Ala Gln Ala
145                 150                 155                 160

Pro Ala Thr Glu Glu Gln Glu Ala Ala Ser Ser Ser Thr Leu Val
                165                 170                 175

Glu Val Thr Leu Gly Glu Val Pro Ala Ala Glu Ser Pro Asp Pro Pro
            180                 185                 190

Gln Ser Pro Gln Gly Ala Ser Ser Leu Pro Thr Thr Met Asn Tyr Pro
        195                 200                 205

Leu Trp Ser Gln Ser Tyr Glu Asp Ser Ser Asn Gln Glu Glu Glu Gly
    210                 215                 220

Pro Ser Thr Phe Pro Asp Leu Glu Ser Glu Phe Gln Ala Ala Leu Ser
225                 230                 235                 240

Arg Lys Val Ala Glu Leu Val His Phe Leu Leu Lys Tyr Arg Ala
                245                 250                 255

Arg Glu Pro Val Thr Lys Ala Glu Met Leu Gly Ser Val Gly Asn
                260                 265                 270

Trp Gln Tyr Phe Phe Pro Val Ile Phe Ser Lys Ala Ser Ser Ser Leu
            275                 280                 285

Gln Leu Val Phe Gly Ile Glu Leu Met Glu Val Asp Pro Ile Gly His
        290                 295                 300

Leu Tyr Ile Phe Ala Thr Cys Leu Gly Leu Ser Tyr Asp Gly Leu Leu
305                 310                 315                 320

Gly Asp Asn Gln Ile Met Pro Lys Ala Gly Leu Leu Ile Ile Val Leu
                325                 330                 335

Ala Ile Ile Ala Arg Glu Gly Asp Cys Ala Pro Glu Glu Lys Ile Trp
                340                 345                 350

Glu Glu Leu Ser Val Leu Glu Val Phe Glu Gly Arg Glu Asp Ser Ile
        355                 360                 365

Leu Gly Asp Pro Lys Lys Leu Leu Thr Gln His Phe Val Gln Glu Asn
    370                 375                 380

Tyr Leu Glu Tyr Arg Gln Val Pro Gly Ser Asp Pro Ala Cys Tyr Glu
385                 390                 395                 400

Phe Leu Trp Gly Pro Arg Ala Leu Val Glu Thr Ser Tyr Val Lys Val
                405                 410                 415

Leu His His Met Val Lys Ile Ser Gly Gly Pro His Ile Ser Tyr Pro
            420                 425                 430
```

```
Pro Leu His Glu Trp Val Leu Arg Glu Gly Glu Gly Gly His His
        435                 440                 445
His His His His His
    450

<210> SEQ ID NO 10
<211> LENGTH: 1362
<212> TYPE: DNA
<213> ORGANISM: Artificial
<220> FEATURE:
<223> OTHER INFORMATION: DNA for fusion protein CLYTA-MAGE3-His

<400> SEQUENCE: 10
atgaaagggg gaattgtaca ttcagacggc tcttatccaa agacaagtt tgagaaaatc      60 aatggcactt ggtactactt tgacagttca ggctatatgc ttgcagaccg ctggaggaag    120
cacacagacg gcaactggta ctggttcgac aactcaggcg aaatggctac aggctggaag    180
aaaatcgctg ataagtggta ctatttcaac gaagaaggtg ccatgaagac aggctgggtc    240
aagtacaagg acacttggta ctacttagac gctaaagaag gcgccatggt atcaaatgcc    300
tttatccagt cagcggacgg aacaggctgg tactacctca aaccgacgg aacactggca    360 gacaggccag aattggccag catgctggac atggatctgg aacagcgtag tcagcactgc    420
aagcctgaaa aggccttga ggcccgagga gaggccctgg gctggtggg tgcgcaggct     480 cctgctactg aggagcagga ggctgcctcc tcctcttcta ctctagttga agtcaccctg    540 gggaggtgc ctgctgccga gtcaccagat cctccccaga gtcctcaggg agcctccagc     600
ctccccacta ccatgaacta ccctctctgg agccaatcct atgaggactc cagcaaccaa    660
gaagaggagg ggccaagcac cttccctgac ctggagtctg agttccaagc agcactcagt    720
aggaaggtgg ccaagttggt tcattttctg ctcctcaagt atcgagccag ggagccggtc    780
acaaaggcag aaatgctggg gagtgtcgtc ggaaattggc agtacttctt cctgtgatc     840 ttcagcaaag cttccgattc cttgcagctg gtctttggca tcgagctgat ggaagtggac    900
cccatcggcc acgtgtacat ctttgccacc tgcctgggcc tctcctacga tggcctgctg    960
ggtgacaatc agatcatgcc caagacaggc ttcctgataa tcatcctggc cataatcgca   1020
aaagagggcg actgtgcccc tgaggagaaa atctgggagg agctgagtgt gttagaggtg   1080
tttgagggga gggaagacag tatcttcggg gatcccaaga agctgctcac ccaatatttc   1140
gtgcaggaaa actacctgga gtaccggcag gtccccggca gtgatcctgc atgctatgag   1200
ttcctgtggg gtccaagggc cctcattgaa accagctatg tgaaagtcct gcaccatatg   1260
gtaaagatca gtggaggacc tcgcatttcc tacccactcc tgcatgagtg ggctttgaga   1320
gagggggaag agggcggtca tcaccatcac catcaccatt aa                      1362

<210> SEQ ID NO 11
<211> LENGTH: 41
<212> TYPE: DNA
<213> ORGANISM: Artificial
<220> FEATURE:
<223> OTHER INFORMATION: MAGE3 p rimer

<400> SEQUENCE: 11
gcgccatgga tctggaacag cgtagtcagc actgcaagcc t                         41

<210> SEQ ID NO 12
<211> LENGTH: 57
<212> TYPE: DNA
<213> ORGANISM: Artificial
```

-continued

```
<220> FEATURE:
<223> OTHER INFORMATION: MAGE3 primer

<400> SEQUENCE: 12
gcgtctagat taatggtgat ggtgatggtg atgaccgccc tcttcccect ctctcaa        57

<210> SEQ ID NO 13
<211> LENGTH: 57
<212> TYPE: DNA
<213> ORGANISM: Artificial
<220> FEATURE:
<223> OTHER INFORMATION: CLYTA primer

<400> SEQUENCE: 13
ttaaaccaca ccttaaggag gatataacat atgaaagggg gaattgtaca ttcagac        57

<210> SEQ ID NO 14
<211> LENGTH: 33
<212> TYPE: DNA
<213> ORGANISM: Artificial
<220> FEATURE:
<223> OTHER INFORMATION: CLYTA primer

<400> SEQUENCE: 14
gccagacatg tccaattctg gcctgtctgc cag                                  33

<210> SEQ ID NO 15
<211> LENGTH: 45
<212> TYPE: DNA
<213> ORGANISM: Artificial
<220> FEATURE:
<223> OTHER INFORMATION: CLYTA primer

<400> SEQUENCE: 15
cccacatgtc cagactgctg gccaattctg gcctgtctgc cagtg                     45

<210> SEQ ID NO 16
<211> LENGTH: 85
<212> TYPE: PRT
<213> ORGANISM: Artificial
<220> FEATURE:
<223> OTHER INFORMATION: MAGE Core signature sequence - consensus
<220> FEATURE:
<221> NAME/KEY: misc_feature
<223> OTHER INFORMATION: Residues 2, 4, 12, 15, 16, 20, 22, 24, 27, 34,
      39, 41, 44, 45, 46, 51, 53, 59, 63, 68, 69, 74, 75, 80, 84 and 85
      may be conservative variants of the amino acid shown.
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
```

<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (47)..(49)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (81)..(83)
<223> OTHER INFORMATION: Xaa can be any naturally occurring amino acid

<400> SEQUENCE: 16

```
Leu Ile Xaa Val Leu Xaa Xaa Ile Xaa Xaa Xaa Gly Xaa Xaa Ala Pro
1               5                   10                  15

Glu Glu Xaa Ile Trp Glu Xaa Leu Xaa Xaa Met Xaa Xaa Xaa Xaa Gly
            20                  25                  30

Xaa Glu Xaa Xaa Xaa Xaa Gly Xaa Pro Xaa Xaa Leu Leu Thr Xaa Xaa
        35                  40                  45

Xaa Val Gln Glu Xaa Tyr Leu Xaa Tyr Xaa Gln Val Pro Xaa Ser Xaa
    50                  55                  60

Pro Xaa Xaa Tyr Glu Phe Leu Trp Gly Pro Arg Ala Xaa Xaa Glu Thr
65                  70                  75                  80

Xaa Xaa Xaa Lys Val
                85
```

PROCESS FOR THE PRODUCTION OF IMMUNOGENIC COMPOSITIONS

CROSS-REFERENCE TO RELATED APPLICATIONS

This application is a continuation of U.S. Ser. No. 09/601,565 filed 3 Aug. 2000 now abandoned (the contents of which are incorporated by reference herein), which is a 371 of PCT/EP99/00660 filed 2 Feb. 1999 (the contents of which are incorporated by reference herein). This application also claims priority to Great Britain applications GB9802543.0 filed on 5 Feb. 1998 and GB9802650.3 filed on 6 Feb. 1998.

STATEMENT REGARDING FEDERALLY SPONSORED RESEARCH OR DEVELOPMENT

Not Applicable

BACKGROUND OF THE INVENTION

The present invention relates to protein derivatives, comprising a tumor-associated antigen, that find utility in cancer vaccine therapy. In particular the derivatives of the invention include fusion proteins comprising an antigen encoded by the family of MAGE genes (e.g. MAGE-3, MAGE-1), linked to an immunological fusion partner which provides T helper epitopes, such as, for example the lipidated form of protein D from *Haemophilus influenzae* B; chemically modified MAGE proteins wherein the antigen's disulphide bridges are reduced and the resulting thiols blocked and genetically modified MAGE proteins provided with an affinity tag and/or genetically modified to prevent disulphide bridge formation. Methods are also described for purifying MAGE proteins and for formulating vaccines for treating a range of cancers, including, but not limited to Melanoma, breast, bladder, lung, NSCLC, head and squamous cell carcinoma, colon carcinoma and oesophagus carcinoma.

Antigens encoded by the family of MAGE genes are predominately expressed on melanoma cells (including malignant melanoma) and some other cancers including NSCLC (non small cell lung cancer), head and neck squamous cell carcinoma, bladder transitional cell carcinoma and oesophagus carcinoma, but are not detectable on normal tissues except in the testis and the placenta (Gaugler, 1994; Weynants, 1994; Patard, 1995). MAGE-3 is expressed in 69% of melanomas (Gaugler, 1994), and can also be detected in 44% of NSCLC (Yoshimatsu 1988), 48% of head and neck squamous cell carcinoma, 34% of bladder transitional cell carcinoma 57% of oesophagus carcinoma 32% of colon cancers and 24% of breast cancers (Van Pel, 1995); Inoue, 1995 Fujie 1997; Nishimura 1997). Cancers expressing MAGE proteins are known as Mage associated tumours.

The immunogenicity of human melanoma cells has been elegantly demonstrated in experiments using mixed cultures of melanoma cells and autologous lymphocytes. These culture often generate specific cytotoxic T lymphocytes (CTLs) able to lyse exclusively the autologous melanoma cells but neither autologous fibroblasts, nor autologous EBV-transformed B lymphocytes (Knuth, 1984; Anichini, 1987). Several of the antigens recognised on autologous melanoma cells by these CTL clones are now identified, including those of the MAGE family.

The first antigen which could be defined through its recognition by specific CTLs on autologous melanoma cells is termed MZ2-E (Van den Eynde, 1989) and is encoded by the gene MAGE-1 (Van der Bruggen, 1991). CTLs directed against MZ2-E recognise and lyse MZ2-E positive melanoma cells from autologous as well as from other patients provided that these cells have the HLA.A1 allele.

The MAGE-1 gene belongs to a family of 12 closely related genes, MAGE 1, MAGE 2, MAGE 3, MAGE 4, MAGE 5, MAGE 6, MAGE 7, MAGE 8, MAGE 9, MAGE 10, MAGE 11, MAGE 12, located on chromosome X and sharing with each other 64 to 85% homology in their coding sequence (De Plaen, 1994). These are sometimes known as MAGE A1, MAGE A2, MAGE A3, MAGE A4, MAGE A5, MAGE A6, MAGE A7, MAGE A8, MAGE A9, MAGE A 10, MAGE A11, MAGE A 12 (The MAGE A family). Two other groups of proteins are also part of the MAGE family although more distantly related. These are the MAGE B and MAGE C group. The MAGE B family includes MAGE B1 (also known as MAGE Xp1, and DAM 10), MAGE B2 (also known as MAGE Xp2 and DAM 6) MAGE B3 and MAGE B4—the Mage C family currently includes MAGE C1 and MAGE C2. In general terms, a MAGE protein can be defined as containing a core sequence signature located towards the C-terminal end of the protein (for example with respect to MAGE A1 a 309 amino acid protein, the core signature corresponds to amino acid 195-279).

The consensus pattern of the core signature is thus described as follows wherein x represents any amino acid, lower case residues are conserved (conservative variants allowed) and upper case residues are perfectly conserved.
Core Sequence Signature (SEQ ID NO: 16)
LixvL(2x)I(3x)g(2x)apEExiWexl(2x)m(3-4x)Gxe(3-4x)gxp(2x)llt(3x)VqexYLxYxqVPxsxP(2x)yeFLWGprA(2x)Et(3x)kv Conservative substitutions are well known and are generally set up as the default scoring matrices in sequence alignment computer programs. These programs include PAM250 (Dayhoft M. O. et al., (1978), "A model of evolutionary changes in proteins", In "Atlas of Protein sequence and structure" 5(3) M. O. Dayhoft (ed.), 345-352), National Biomedical Research Foundation, Washington, and Blosum 62 (Steven Henikoft and Jorja G. Henikoft (1992), "Amino acid substitution matricies from protein blocks"), Proc. Natl. Acad. Sci. USA 89 (Biochemistry): 10915-10919.

In general terms, substitution within the following groups are conservative substitutions, but substitutions between groups are considered non-conserved. The groups are:
 i) Aspartate/asparagine/glutamate/glutamine
 ii) Serine/threonine
 iii) Lysine/arginine
 iv) Phenylalanine/tyrosine/tryptophane
 v) Leucine/isoleucine/valine/methionine
 vi) Glycine/alanine In general and in the context of this invention, a MAGE protein will be approximately 50% identical in this core region with amino acids 195 to 279 of MAGE A1.

Several CTL epitopes have been identified on the MAGE-3 protein. One such epitope, MAGE-3.A1, is a nonapeptide sequence located between amino acids 168 and 176 of the MAGE-3 protein which constitutes an epitope specific for CTLs when presented in association with the MHC class I molecule HLA.A1. Recently two additional CTL epitopes have been identified on the peptide sequence of the MAGE-3 protein by their ability to mount a CTL response in a mixed culture of melanoma cells and autologous lymphocytes.

These two epitopes have specific binding motifs for the HLA.A2 (Van der Bruggen, 1994) and HLA.B44 (Herman, 1996) alleles respectively.

BRIEF SUMMARY OF THE INVENTION

The present invention provides MAGE protein derivatives. Such derivatives are suitable for use in therapeutic vaccine formulations which are suitable for the treatment of a range of tumour types.

DETAILED DESCRIPTION OF THE INVENTION

Figure 1:
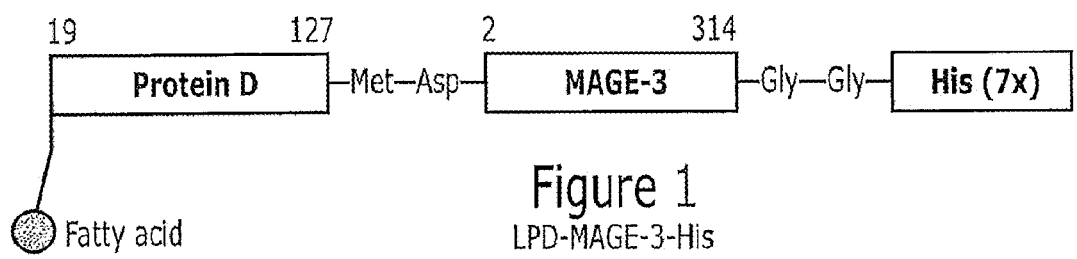
FIG. 1: LPD-MAGE-3-His

In one embodiment of the present invention, the derivative is a fusion proteins comprising an antigen from the MAGE protein family linked to a heterologous partner. The proteins may be chemically conjugated, but are preferably expressed as recombinant fusion proteins allowing increased levels to be produced in an expression system as compared to non-fused protein. Thus the fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

In a preferred form of the invention, the immunological fusion partner is derived from protein D, a surface protein of the gram-negative bacterium, *Haemophilus influenza* B (WO91/18926). Preferably the protein D derivative comprises approximately the first 1/3 of the protein, in particular approximately the first N-terminal 100-110 amino acids. Preferably the protein D derivative is lipidated. Preferably the first 109 residues of the Lipoprotein D fusion partner is included on the N-terminus to provide the vaccine candidate antigen with additional exogenous T-cell epitopes and increase expression level in *E-coli* (thus acting also as an expression enhancer). The lipid tail ensures optimal presentation of the antigen to antigen presenting cells.

Other fusion partners include the non-structural protein from influenzae virus, NS1 (hemagglutinin). Typically the N terminal 81 amino acids are utilised, although different fragments may be used provided they include T-helper epitopes.

In another embodiment the immunological fusion partner is the protein known as LYTA. Preferably the C terminal portion of the molecule is used. Lyta is derived from *Streptococcus pneumoniae* which synthesize an N-acetyl-L-alanine amidase, amidase LYTA, (coded by the lytA gene {Gene, 43 (1986) page 265-272} an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at its amino terminus has been described {Biotechnology: 10, (1992) page 795-798}. As used herein a preferred embodiment utilises the repeat portion of the Lyta molecule found in the C terminal end starting at residue 178. A particularly preferred form incorporates residues 188-305.

The immunological fusion partners noted above are also advantageous in aiding expression. In particular, such fusions are expressed at higher yields than native recombinant MAGE proteins.

Such constructs in a clinical setting have been shown by the present inventors to be able to treat melanoma. In one case, a patient with stage IV melanoma was cleared of metasties after two doses of unadjuvanted lipo D 1/3 MAGE 3 His protein.

Accordingly, the present invention in the embodiment provides fusion proteins comprising a tumour-associated antigen from the MAGE family linked to an immunological fusion partner. Preferably the immunological fusion partner is protein D or fragment thereof, most preferably lipoprotein D. The MAGE proteins are preferably MAGE A1 or MAGE A3. The Lipoprotein D part preferably comprises the first 1/3 of Lipoprotein D.

The proteins of the present invention preferably are expressed in *E. coli*. In a preferred embodiment the proteins are expressed with an affinity tag, such as for example, a histidine tail comprising between 5 to 9 and preferably six histidine residues. These are advantageous in aiding purification.

The present invention also provides a nucleic acid encoding the proteins of the present invention. Such sequences can be inserted into a suitable expression vector and used for DNA/RNA vaccination or expressed in a suitable host. Microbial vectors expressing the nucleic acid may be used as vaccines. Such vectors include for example, poxvirus, adenovirus, alphavirus, listeria and monarphage.

A DNA sequence encoding the proteins of the present invention can be synthesized using standard DNA synthesis techniques, such as by enzymatic ligation as described by D. M. Roberts et al. in Biochemistry 1985, 24, 5090-5098, by chemical synthesis, by in vitro enzymatic polymerization, or by PCR technology utilising for example a heat stable polymerase, or by a combination of these techniques.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°-37° C., generally in a volume of 50 µl or less. Enzymatic ligation of DNA fragments may be carried out using a DNA ligase such as T4 DNA ligase in an appropriate buffer, such as 0.05M Tris (pH 7.4), 0.01M $MgCl_2$, 0.01M dithiothreitol, 1 mM spermidine, 1 mM ATP and 0.1 mg/ml bovine serum albumin, at a temperature of 4° C. to ambient, generally in a volume of 50 ml or less. The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes, M. Singh, B. S. Sproat, and R. C. Titmas, Nucleic Acids Research, 1982, 10, 6243; B. S. Sproat, and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus, and H. Koester, Nucleic Acids Research, 1984, 12, 4539; and H. W. D. Matthes et al., EMBO Journal, 1984, 3, 801.

The process of the invention may be performed by conventional recombinant techniques such as described in Maniatis et al., Molecular Cloning—A Laboratory Manual; Cold Spring Harbor, 1982-1989.

In particular, the process may comprise the steps of:
i) preparing a replicable or integrating expression vector capable, in a host cell, of expressing a DNA polymer comprising a nucleotide sequence that encodes the protein or an immunogenic derivative thereof;
ii) transforming a host cell with said vector;
iii) culturing said transformed host cell under conditions permitting expression of said DNA polymer to produce said protein; and
iv) recovering said protein.

The term 'transforming' is used herein to mean the introduction of foreign DNA into a host cell. This can be achieved for example by transformation, transfection or infection with an appropriate plasmid or viral vector using e.g. conventional techniques as described in Genetic Engineering; Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest.

The expression vectors are novel and also form part of the invention.

The replicable expression vectors may be prepared in accordance with the invention, by cleaving a vector compatible with the host cell to provide a linear DNA segment having an intact replicon, and combining said linear segment with one or more DNA molecules which, together with said linear segment encode the desired product, such as the DNA polymer encoding the protein of the invention, or derivative thereof, under ligating conditions.

Thus, the DNA polymer may be preformed or formed during the construction of the vector, as desired.

The choice of vector will be determined in part by the host cell, which may be prokaryotic or eukaryotic but are preferably E. Coli or CHO cells. Suitable vectors include plasmids, bacteriophages, cosmids and recombinant viruses.

The preparation of the replicable expression vector may be carried out conventionally with appropriate enzymes for restriction, polymerisation and ligation of the DNA, by procedures described in, for example, Maniatis et al. cited above.

The recombinant host cell is prepared, in accordance with the invention, by transforming a host cell with a replicable expression vector of the invention under transforming conditions. Suitable transforming conditions are conventional and are described in, for example, Maniatis et al. cited above, or "DNA Cloning" Vol. II, D. M. Glover ed., IRL Press Ltd, 1985.

The choice of transforming conditions is determined by the host cell. Thus, a bacterial host such as E. coli may be treated with a solution of $CaCl_2$ (Cohen et al., Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells. The invention also extends to a host cell transformed with a replicable expression vector of the invention.

Culturing the transformed host cell under conditions permitting expression of the DNA polymer is carried out conventionally, as described in, for example, Maniatis et al. and "DNA Cloning" cited above. Thus, preferably the cell is supplied with nutrient and cultured at a temperature below 50° C.

The product is recovered by conventional methods according to the host cell and according to the localisation of the expression product (intracellular or secreted into the culture medium or into the cell periplasm). Thus, where the host cell is bacterial, such as E. coli it may, for example, be lysed physically, chemically or enzymatically and the protein product isolated from the resulting lysate. Where the host cell is mammalian, the product may generally be isolated from the nutrient medium or from cell free extracts. Conventional protein isolation techniques include selective precipitation, adsorption chromatography, and affinity chromatography including a monoclonal antibody affinity column.

The proteins of the present invention are provided either soluble in a liquid form or in a lyophilised form.

It is generally expected that each human dose will comprise 1 to 1000 µg of protein, and preferably 30-300 µg.

The present invention also provides pharmaceutical composition comprising a protein of the present invention in a pharmaceutically acceptable excipient.

A preferred vaccine composition comprises at least Lipoprotein D-MAGE-3. Such vaccine may optionally contain one or more other tumor-associated antigen. For example other members belonging to the MAGE and GAGE families. Suitable other tumour associated antigen include MAGE-1, GAGE-1 or Tyrosinase proteins.

Vaccine preparation is generally described in Vaccine Design ("The subunit and adjuvant approach" (eds. Powell M. F. & Newman M. J). (1995) Plenum Press New York). Encapsulation within liposomes is described by Fullerton, U.S. Pat. No. 4,235,877.

The proteins of the present invention are preferably adjuvanted in the vaccine formulation of the invention. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes. Other known adjuvants include CpG containing oligonucleotides. The oligonucleotides are characterised in that the CpG dinucleotide is unmethylated. Such oligonucleotides are well known and are described in, for example WO96/02555.

In the formulation of the inventions it is preferred that the adjuvant composition induces an immune response preferentially of the TH1 type. Suitable adjuvant systems include, for example a combination of monophosphoryl lipid A, preferably 3-de-O-acylated monophosphoryl lipid A (3D-MPL)

together with an aluminium salt. CpG oligonucleotides also preferentially induce a TH1 response.

An enhanced system involves the combination of a monophosphoryl lipid A and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21 3D-MPL & tocopherol in an oil in water emulsion is described in WO 95/17210 and is a preferred formulation.

Accordingly in one embodiment of the present invention there is provided a vaccine comprising a protein of the present invention, more preferably a Lipoprotein D (or derivative thereof)-MAGE-3 adjuvanted with a monophosphoryl lipid A or derivative thereof.

Preferably the vaccine additionally comprises a saponin, more preferably QS21.

Preferably the formulation additional comprises an oil in water emulsion and tocopherol. The present invention also provides a method for producing a vaccine formulation comprising mixing a protein of the present invention together with a pharmaceutically acceptable excipient, such as 3D-MPL.

In one aspect of the invention there is provided a process for purifying a recombinantly produced MAGE-protein. The process comprises solubilising the protein, for example in a strong chaotropic agent (such as for example, urea, guanidium hydrochloride), or in a Zwitterionicnic detergent, e.g. (Empigen BB—n-dodecyl-N,N-dimethylglycine), reducing the protein's intra and inter molecular disulphide bonds, blocking the resulting thiols to prevent oxidative recoupling, and subjecting the protein to one or more chromatographic steps.

Preferably, the blocking agent is an alkylating agent. Such blocking agents include but are not limited to alpha haloacids or alpha haloamides. For example iodoacetic acid and iodoacetamide which results in carboxymethylation or carboxyamidation (carbamidomethylation) of the protein. Other blocking agents may be used and are described in the literature (See for example, The Proteins Vol II Eds H neurath, R L Hill and C-L Boeder, Academic press 1976, or Chemical Reagents for Protein modification Vol I eds. R L Lundblad and C M Noyes, CRC Press 1985). Typical examples of such other blocking agents include N-ethylmaleimide, chloroacetyl phosphate, O-methylisourea and acrylonitrile. The use of the blocking agent is advantageous as it prevents aggregation of the product, and ensure stability for downstream purification.

In an embodiment of the invention the blocking agents are selected to induce a stable covalent and irreversible derivative (eg alpha halo acids or alpha haloamides). However other blocking agents maybe selected such that after purification the blocking agent may be removed to release the non derivatised protein.

MAGE proteins having derivatised free thiol residues are new and form an aspect of the invention. In particular carboxyamidated or carboxymethylated derivatives are a preferred embodiment of the invention.

In a preferred embodiment of the invention the proteins of the present invention is provided with an affinity tag, such as CLYTA or a polyhistidine tail. In such cases the protein after the blocking step is preferably subjected to affinity chromatography. For those proteins with a polyhistidine tail, immobilised metal ion affinity chromatography (IMAC) may be performed. The metal ion, may be any suitable ion for example zinc, nickel, iron, magnesium or copper, but preferably zinc or nickel. Preferably the IMAC buffer contain a zwitterionic detergent such as Empigen BB (hereinafter Empigen) as this results in lower levels of endotoxin in the final product.

If the protein is produced with a Clyta part, the protein may be purified by exploiting its affinity to choline or choline analogues such as DEAE. In an embodiment of the invention the proteins are provided with a polyhistidine tail and a Clyta part. These may purified in a simple two step affinity chromatographic purification schedule.

The invention will be further described by reference to the following examples:

EXAMPLE I

Preparation of the Recombinant *E. coli* Strain Expressing the Fusion Protein Lipoprotein D-MAGE-3-His (LPD 1/3-MAGE-3-His or LpD MAGE-3His)

1. The *E. Coli* Expression System:

For the production of Lipoprotein D the DNA encoding protein D has been cloned into the expression vector pMG 81. This plasmid utilizes signals from lambda phage DNA to drive the transcription and translation of inserted foreign genes. The vector contains the lambda PL promoter PL, operator OL and two utilization sites (NutL and NutR) to relieve transcriptional polarity effects when N protein is provided (Gross et al., 1985. Mol. & Cell. Biol. 5:1015). Vectors containing the PL promoter, are introduced into an *E. coli* lysogenic host to stabilize the plasmid DNA. Lysogenic host strains contain replication-defective lambda phage DNA integrated into the genome (Shatzman et al., 1983; In Experimental Manipulation of Gene Expression. Inouya (ed) pp 1-14. Academic Press NY). The lambda phage DNA directs the synthesis of the cI repressor protein which binds to the OL repressor of the vector and prevents binding of RNA polymerase to the PL promoter and thereby transcription of the inserted gene. The cI gene of the expression strain AR58 contains a temperature sensitive mutation so that PL directed transcription can be regulated by temperature shift, i.e. an increase in culture temperature inactivates the repressor and synthesis of the foreign protein is initiated. This expression system allows controlled synthesis of foreign proteins especially of those that may be toxic to the cell (Shimataka & Rosenberg, 1981. Nature 292:128).

2. The *E. Coli* Strain AR58:

The AR58 lysogenic *E. coli* strain used for the production of the LPD-MAGE-3-His protein is a derivative of the standard NIH *E. coli* K12 strain N99 (F-su-galK2, lacZ-thr-). It contains a defective lysogenic lambda phage (galE::TN10, 1 Kil-cI857 DH1). The Kil-phenotype prevents the shut off of host macromolecular synthesis. The cI857 mutation confers a temperature sensitive lesion to the cI repressor. The DH1 deletion removes the lambda phage right operon and the hosts bio, uvr3, and chlA loci. The AR58 strain was generated by transduction of N99 with a P lambda phage stock previously grown on an SA500 derivative (galE::TN10, 1 Kil-cI857 DH1). The introduction of the defective lysogen into N99 was selected with tetracycline by virtue of the presence of a TN10 transposon coding for tetracyclin resistance in the adjacent galE gene. N99 and SA500 are *E. coli* K12 strains derived from Dr. Martin Rosenberg's laboratory at the National Institutes of Health.

3. Construction of the Vector Designed to Express the Recombinant Protein LPD-MAGE-3-His:

The rationale was to express MAGE 3 as a fusion protein using the N-terminal third of the lipidated protein D as fusion partner connected at the N-terminus of MAGE-3 and a sequence of several histidine residues (His tail) placed at its C-terminus Protein D is a lipoprotein (a 42 kDa immunoglobulin D binding protein exposed on the surface of the Gram-negative bacterium *Haemophilus influenzae*). The protein is synthesized as a precursor with an 18 amino acid residue signal sequence, containing a consensus sequence for bacterial lipoprotein (WO 91/18926).

When the signal sequence of a lipoprotein is processed during secretion, the Cys (at position 19 in the precursor molecule) becomes the amino terminal residue and is concomitantly modified by covalent attachment of both ester-linked and amide-linked fatty acids.

The fatty acids linked to the amino-terminal cysteine residue then function as membrane anchor.

The plasmid expressing the fusion protein was designed to express a precursor protein containing the 18 amino acids signal sequence and the first 109 residues of the processed protein D, two unrelated amino acids (Met and Asp), amino acid residues 3 to 314 of MAGE-3, two Gly residues functioning as a hinge region to expose the subsequent seven His residues. (SEQ ID NO:2 encoded by SEQ ID NO:1)

The recombinant strain thus produces the processed lipidated His tailed fusion protein of 432 amino acid residues long (see FIG. 1), with the amino acids sequence described in SEQ ID NO:2 and the coding sequence is described in SEQ ID NO:1.

Figure 2:
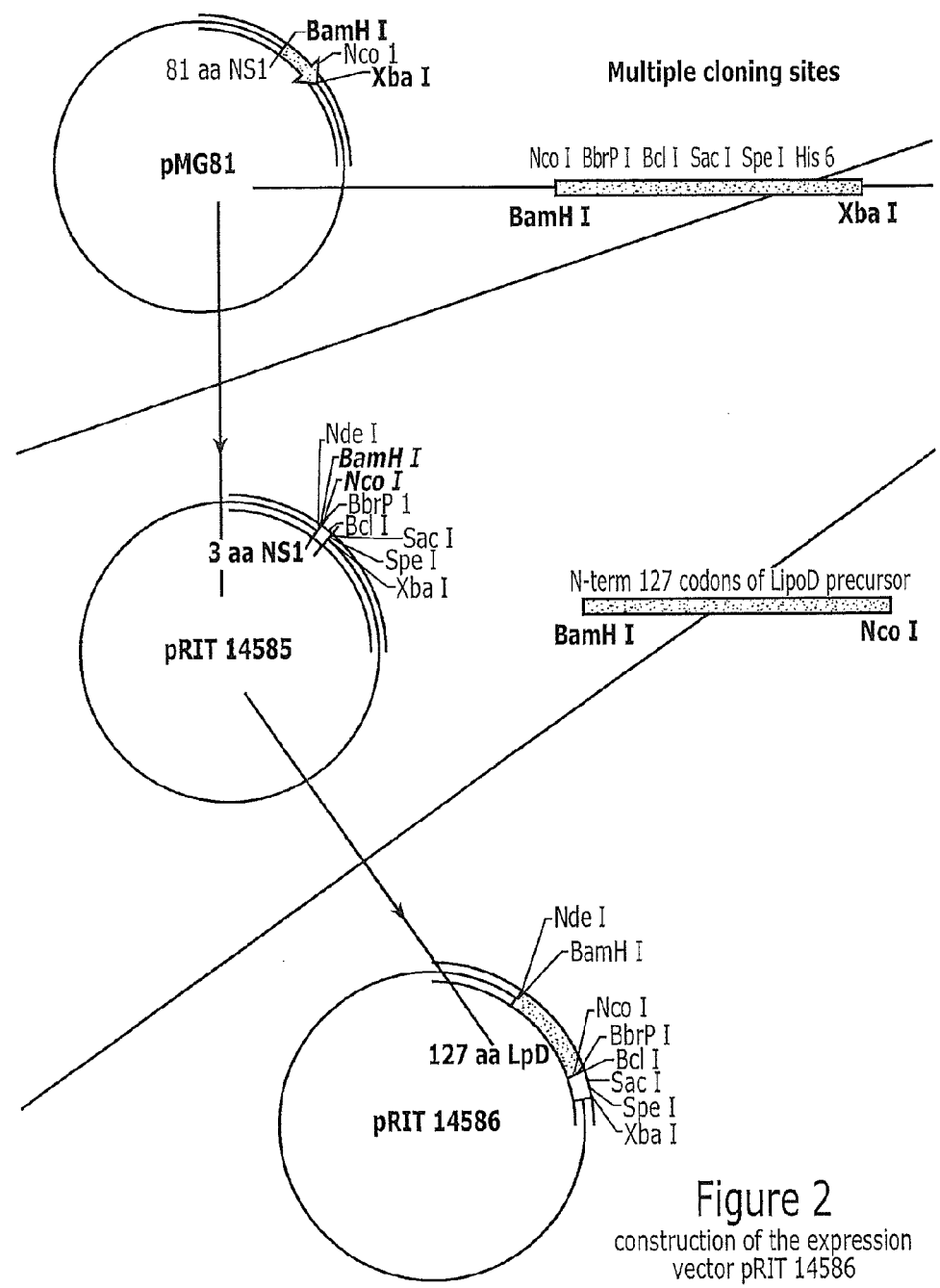
FIG. 2: Construction of the Expression Vector pRIT 14586
Figure 3:
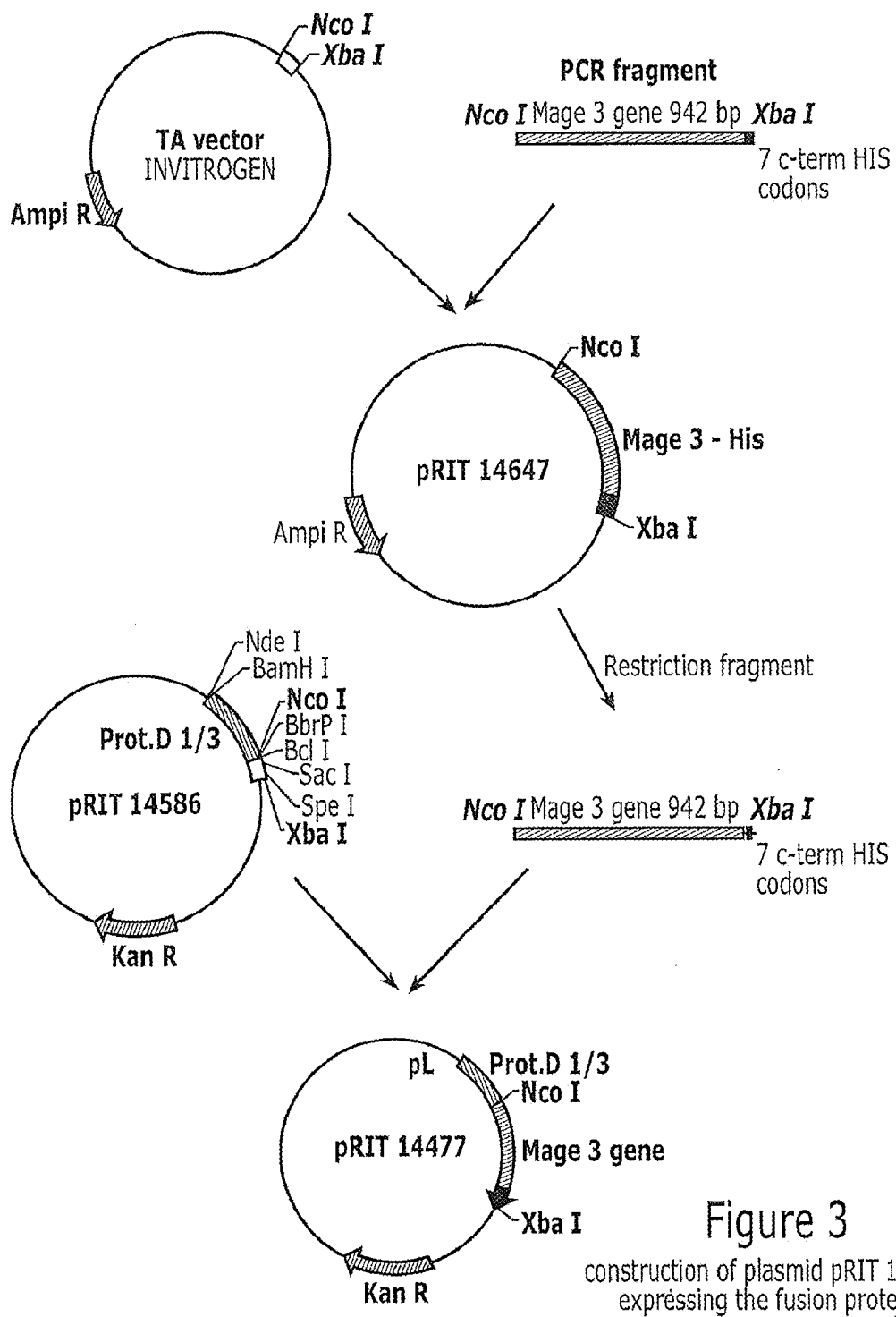
FIG. 3: Construction of the plasmid pRIT 14477 expressing the fusion protein Prot. D 1/3 MAGE-3-His tail

4. Cloning Strategy for the Generation of the LPD-MAGE-3-His Fusion Protein (Vector pRIT14477):

A cDNA plasmid (from Dr Thierry Boon from the Ludwig Institute) containing the coding sequence for MAGE-3 gene (Gaugler B et al, 1994), and the vector PRIT 14586, containing the N terminal portion of the Lipo-D-1/3 coding sequence (prepared as outlined in FIG. 2) were used. The cloning strategy included the following steps (FIG. 3).

a)—PCR amplification of the sequences presented in the plasmid cDNA MAGE 3 using the oligonucleotide sense: 5' gc gcc atg gat ctg gaa cag cgt agt cag cac tgc aag cct (SEQ ID NO:11), and the oligonucleotide antisense: 5' gcg tct aga tta atg gtg atg gtg atg gtg atg acc gcc ctc ttc ccc ctc tct caa (SEQ ID NO:12); this amplification leads to the following modifications at the N terminus: changing of the first five codons to *E. coli* codon usage, replacement of the Pro codon by an Asp codon at position 1, installation of an NcoI site at the 5' extremity and finally addition of two 2 Gly codons and the 7 His codon followed by an XbaI site at the C-terminus.

b)—Cloning into the TA cloning vector of invitrogen of the above amplified fragment and preparation of the intermediate vector pRIT14647.

c)—Excision of the NcoI XbaI fragment from plasmid pRIT14647 and cloning into the vector pRIT 14586.

d)—Transformation of the host strain AR58.

e)—Selection and characterization of the *E. coli* strain transformants containing the plasmid pRIT 14477, expressing the LPD-MAGE-3-His fusion protein.

EXAMPLE II

Preparation of the LPD1/3-MAGE-3-His Antigen

1. Growth and Induction of Bacterial Strain—Expression of LPD1/3-MAGE-3-His:

Cells of AR58 transformed with plasmid pRIT14477 were grown in 2 liter flasks, each containing 400 mL of LY12 medium supplemented with yeast extract (6.4 g/L) and kanamycin sulphate (50 mg/L). After incubation on a shaking table at 30° C. for 8+/−1 h, a small sample was removed from each flask for microscopic examination. The contents of the two flasks were pooled to provide the inoculum for the 20 liter fermentor.

The inoculum (about 800 mL) was added to a pre-sterilised 20 liter (total volume) fermentor containing 7 liters of medium, supplemented with 50 mg/L of kanamycin sulphate. The pH was adjusted to and maintained at 6.8 by the periodic addition of $NH_4OH$ (25% v/v), and the temperature was adjusted to and maintained at 30° C. The aeration rate was adjusted to and maintained at 12 liters of air/min and the dissolved oxygen tension was maintained at 50% of saturation by feedback control of the agitation speed. The overpressure in the fermentor was maintained at 500 g/cm² (0.5 bar).

The fed-batch cultivation was carried out by controlled addition of a carbon feed solution. The feed solution was added at an initial rate of 0.04 mL/min, and increased exponentially during the first 42 hours to maintain a growth rate of $0.1\ h^{-1}$.

After 42 hours, the temperature in the fermentor was rapidly increased to 39° C., and the feeding speed was maintained constant at 0.005 mL/g DCW/min during the induction phase for an additional 22-23 hours, during which time intracellular expression of LPD-MAGE-3-His reached a maximum level.

Aliquots (15 mL) of broth were taken at regular intervals throughout the growth/induction phases and at the end of the fermentation to follow the kinetics of microbial growth and intracellular product expression and in addition, to provide samples for microbial identification/purity tests.

At the end of fermentation, the optical density of the culture was between 80 and 120 (corresponding to a cell concentration of between 48 and 72 g DCW/L), and the total liquid volume was approximately 12 liters. The culture was rapidly cooled to between 6 and 10° C., and the cells of ECK32 were separated from the culture broth by centrifugation at 5000×g at 4° C. for 30 minutes. The concentrated cells of ECK32 were quickly stored in plastic bags and immediately frozen at −80° C.

2. Extraction of the Protein:

The frozen concentrated cells of ECK32 were thawed to 4° C. before being re-suspended in cell disruption buffer to a final optical density of 60 (corresponding to a cell concentration of approximately 36 g DCW/L).

The cells were disrupted by two passes through a high-pressure homogeniser (1000 bar). The broken cell suspension was centrifuged (×10 000 g at 4° C. for 30 minutes) and the pellet fraction was washed twice with Triton X100 (1% w/v)+ EDTA (1 mM), followed by a wash with phosphate buffered saline (PBS)+Tween 20 (0.1% v/v) and finally a wash with PBS. Between each washing stage, the suspension was centrifuged at ×10 000 g for 30 minutes at 4° C., the supernatant was discarded and the pellet fraction was retained.

EXAMPLE III

Characterisation of Fusion Protein Lipo D-MAGE 3

1. Purification:

LPD-MAGE-3-His was purified from the cell homogenate using a sequence of steps described below:

a)—Solubilisation of the washed pellet fraction from cell disruption, b)—Chemical reduction of intra- and inter-protein disulphide bonds followed by blocking of thiol groups to prevent oxidative re-coupling, c)—Microfiltration of the reaction mixture for the removal of particulates and reduction of endotoxins,
d)—Capture and primary purification of LPD-MAGE-3-His by exploitation of the affinity interaction between the polyhistidine tail and zinc-loaded Chelating Sepharose,
e)—Removal of contaminant proteins by anion exchange chromatography.

The purified LPD-MAGE 3-His was subjected to a number of polishing stages:
f)—Buffer exchange/urea removal by size exclusion chromatography using Superdex 75,
g)—In-process filtration,
h)—Buffer exchange/desalting by size exclusion chromatography using Sephadex G25.

Each of these steps is described in more detail below:

1.1)—Solubilisation of Cell Homogenate Pellet

The pellet fraction from the final washing stage (as described above) was re-solubilised overnight in 800 mL of a solution of guanidine hydrochloride (6M) and sodium phosphate (0.1 M, pH 7.0) at 4° C.

1.2)—Reduction and Carboxymethylation

The solubilised material (a pale yellow, turbid suspension) was flushed with argon to purge any remaining oxygen, and a stock solution of 2-mercaptoethanol (14M) was added to provide a final concentration of 4.3M (which corresponded to 0.44 mL of 2-mercaptoethanol per mL of solution).

The resulting solution was divided and transferred into two glass flasks which were both heated to 95° C. in a water bath. After 15 minutes at 95° C., the flasks were removed from the water bath and allowed to cool, whereupon the contents were pooled into a foil-covered beaker (5 L), placed on ice, and solid iodoacetamide added with vigorous mixing to provide a final concentration of 6M (which corresponded to 1.11 g of iodoacetamide per mL of solution). The mixture was held on ice in the dark for 1 hour to ensure complete solubilisation of iodoacetamide, before being neutralised (maintaining vigorous mixing and continuous pH monitoring) by the addition of approximately 1 liter of sodium hydroxide (5 M) to give a final pH of 7.5-7.8.

The resulting mixture was maintained on ice in the dark for a further 30 minutes, after which time the pH was re-adjusted to pH 7.5-7.8.

1.3)—Microfiltration

The mixture was microfiltered in an Amicon Proflux M12 tangential-flow unit equipped with a Minikros hollow fibre cartridge (ref No. M22M-600-01N; area 5,600 cm$^2$, 0.2 μm). The permeate was retained for subsequent chromatographic purification.

1.4)—Metal ($Zn^{2+}$) Chelate Chromatography (IMAC)

Metal chelate chromatography was performed with Chelating Sepharose FF (Pharmacia Biotechnology Cat. No. 17-0575-01) packed into a BPG 100/500 column (Pharmacia Biotechnology Cat No. 18-1103-01). The dimensions of the packed bed were: diameter 10 cm; cross-sectional area 79 cm$^2$; bed height 19 cm; packed volume 1,500 mL. The empty column was sanitised with sodium hydroxide (0.5M), then washed with purified water.

The support (delivered in 20% v/v ethanol) was washed with purified water (8 liters) on a Buchner funnel (under vacuum) and charged with zinc by passing at least 15 liters of a solution of $ZnCl_2$ (0.1M). Excess zinc was removed by washing the support with 10 liters of purified water, until the pH of the outlet liquid reached the pH of the $ZnCl_2$ solution (pH 5.0). The support was then equilibrated with 4 liters of a solution containing guanidine hydrochloride (6M) and sodium phosphate (0.1M, pH 7.0).

The permeate from microfiltration, containing LPD-MAGE-3-His, was mixed with the support (batch binding), before loading and packing the BPG column with the solution containing guanidine hydrochloride (6M) and sodium phosphate (0.1M, pH 7.0).

The next stages of metal chelate chromatography were conducted at an eluent flow rate of 60 mL/min. The column was washed, first with the solution containing guanidine hydrochloride (6M) and sodium phosphate (0.1M, pH 7.0), then with the solution containing urea (6M) and sodium phosphate (0.1M, pH 7.0), until the column eluent attained zero absorbance at $OD_{280}$ nm (baseline).

The semi-pure LPD-MAGE-3-His protein fraction was eluted with 2 column volumes of a solution containing urea (6M), sodium phosphate (0.1M, pH 7.0) and imidazole (0.5M). The conductance of this fraction was approximately 16 mS/cm.

1.5)—Anion Exchange Chromatography

Before continuing with anion exchange chromatography, the conductance of the semi-pure LPD-MAGE-3-His protein fraction was reduced to approximately 4 mS/cm by dilution with a solution containing urea (6M) and Tris-HCl (20 mM, pH 8.0).

Anion exchange chromatography was performed using Q-Sepharose FF (Pharmacia Biotechnology, Cat. No. 17-0510-01) packed in a BPG 200/500 column (Pharmacia Biotechnology Cat. No. 18-1103-11). The dimensions of the packed bed were: diameter 10 cm; cross-sectional area 314 cm$^2$; bed height 9 cm; packed volume 2,900 mL.

The column was packed (with 20% v/v ethanol) and washed with 9 liters of purified water at an eluent flow rate of 70 mL/min. The packed column was sanitised with 3 liters of sodium hydroxide (0.5M), washed with 30 liters of purified water, then equilibrated with 6 liters of a solution containing urea (6M) and Tris-HCl (20 mM, pH 8.0). The diluted, semi-purified LPD-MAGE-3-His was loaded onto the column and then washed with 9 liters of a solution containing urea (6M), Tris-HCl (20 mM, pH 8.0), EDTA (1 mM) and Tween (0.1%), until the absorbance (280 nm) of the eluent fell to zero.

A further washing step was performed with 6 liters of a solution containing urea (6M) and Tris-HCl (20 mM, pH 8.0).

The purified LPD-MAGE-3-His was eluted from the column with a solution containing urea (6M), Tris-HCl (20 mM, pH 8.0) and NaCl (0.25M).

1.6)—Size Exclusion Chromatography

The removal of urea from purified LPD-MAGE-3-His and the buffer exchange were both achieved by size exclusion chromatography. This was performed using Superdex 75 (Pharmacia Biotechnology Cat. No. 17-1044-01) packed in an XK 50/100 column (Pharmacia Biotechnology Cat. No. 18-8753-01). The dimensions of the packed bed were: diameter 5 cm; cross-sectional area 19.6 cm$^2$; bed height 90 cm; packed volume 1,800 mL.

The column was packed in ethanol (20%) and washed with 5 liters of purified water at an effluent flow rate of 20 mL/min. The column was sanitised with 2 liters of sodium hydroxide (0.5M), washed with 5 liters of purified water, then equilibrated with 5 liters of phosphate-buffered saline containing Tween 80 (0.1% v/v).

The purified LPD-MAGE-3-His fraction (maximum 500 mL/desalting run) was loaded onto the column at an eluent flow rate of 20 mL/min. The desalted purified LPD-MAGE-3-His was eluted from the column with 3 liters of PBS containing Tween 80 (0.1% v/v).

The fraction containing LPD-MAGE-3-His eluted at the void volume of the column.

1.7)—In-process Filtration

The bulk LPD-MAGE-3-His from size exclusion chromatography was filtered through a 0.22 μm membrane in a laminar flow hood (class 10.000). The filtered bulk was frozen at −80° C. and stored until the desalting step.

1.8)—Desalting Chromatography

Since the osmolality of the final bulk should be less than 400 mOsM, a further buffer exchange step was required to reduce the salt concentration. This was performed by a desalting chromatographic step using Sephadex G25 (Pharmacia Biotechnology Cat. No. 17-0033-02) packed in a BPG 100/950 column (Pharmacia Biotechnology Cat. No. 18-1103-03). The dimensions of the packed bed were: diameter 10 cm; cross-sectional area 78.6 $cm^2$; bed height 85 cm; packed volume 6,500 mL.

The Sephadex G25 was hydrated with 7 liters of purified water and allowed to swell overnight at 4° C. The gel was then packed in the column with pure water at an eluent flow rate of 100 mL/min.

The column was sanitised with 6 liters of sodium hydroxide (0.5M), then equilibrated with 10 liters of a solution containing sodium phosphate (10 mM, pH 6.8), NaCl (20 mM) and Tween 80 (0.1% v/v).

The purified LPD-MAGE-3-His fraction (maximum 1500 mL/desalting run) was loaded onto the column at an eluent flow rate of 100 mL/min. The desalted purified LPD-MAGE-3-His fraction eluted at the void volume of the column, was sterile filtered through a 0.22 μm membrane and stored at −80° C.

The final bulk protein is thawed to +4° C. before being aliquoted into vials and freeze-dried in a lactose excipient (3.2%).

2. Analysis on Coomassie-stained SDS-polyacrylamide Gels:

The LPD-MAGE-3-His purified antigen was analysed by SDS-PAGE on a 12.5% acrylamide gel in reducing conditions.

The protein load was 50 μg for Coomassie blue staining and 5 μg for silver nitrate staining Clinical lot 96K19 and pilot lot 96J22 were analyzed. One major band corresponding to a molecular weight of 60 kDa was visualised. Two minor additional bands of approximately 45 kDa and 35 kDa were also seen.

3. Western Blot Analysis:

The peptides revealed by SDS-PAGE analysis of the LPD-MAGE-3-His protein were identified by Western blot using mouse monoclonal antibodies. These antibodies were developed in-house using a purified preparation of the MAGE-3-His protein (this protein does not contain the LPD part of the LPD-MAGE-3-His).

Figure 4:
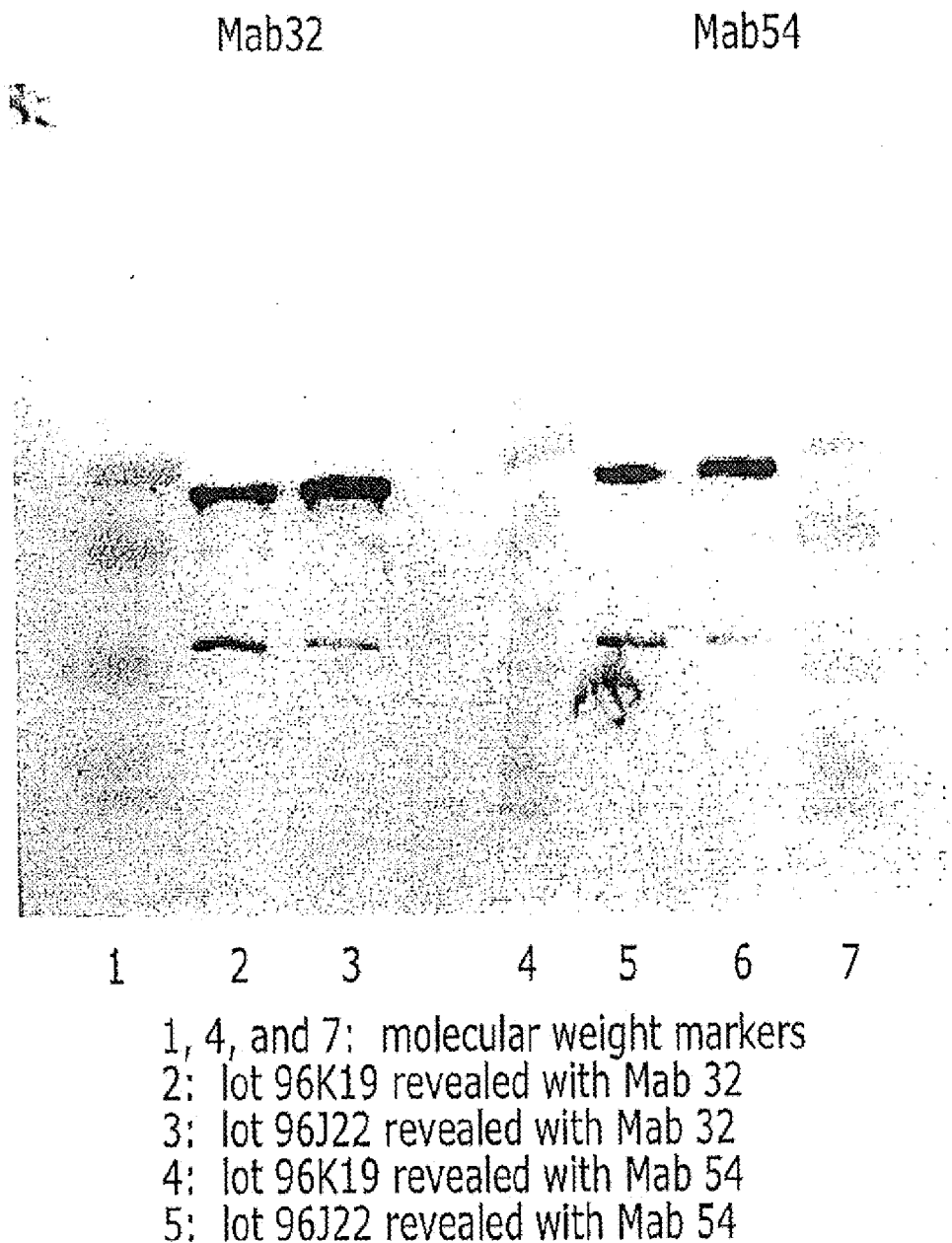
FIG. 4: Western blot analysis of LPD-MAGE-3-His protein Anti-MAGE-3 monoclonal antibodies Mab 32 and Mab 54
FIG. 5. Immunogenicity of MAGE-3 in mice (C57BL6)

Two monoclonal antibody preparations (Mab 22 and Mab 54) have been selected on the basis of their suitability for Western blot analysis and used in the identity test for lot release. FIG. 4 shows the band patterns obtained for lots 96K19 and 96J22 after staining with Mabs 32 and 54. Six hundred (600) ng of protein were resolved on a 12.5% SDS-PAGE, transferred to a nylon membrane, reacted with Mabs 32 and 54 (60 μg/ml) and revealed with anti-mouse antibodies coupled to peroxidase.

The 60 kDa and 30 kDa peptide detected by SDS-PAGE are revealed by both Mabs.

EXAMPLE IV

1. Vaccine Preparation Using LPD-MAGE-3-His Protein:

The vaccine used in these experiments is produced from a recombinant DNA, encoding a Lipoprotein D 1/3-MAGE-3-His, expressed in *E. coli* from the strain AR58, either adjuvanted or not. As an adjuvant, the formulation comprises a mixture of 3 de —O-acylated monophosphoryl lipid A (3D-MPL) and QS21 in an oil/water emulsion. The adjuvant system SBAS2 has been previously described WO 95/17210.

3D-MPL: is an immunostimulant derived from the lipopolysaccharide (LPS) of the Gram-negative bacterium *Salmonella minnesota*. MPL has been deacylated and is lacking a phosphate group on the lipid A moiety. This chemical treatment dramatically reduces toxicity while preserving the immunostimulant properties (Ribi, 1986). Ribi Immunochemistry produces and supplies MPL to SB-Biologicals.

Experiments performed at Smith Kline Beecham Biologicals have shown that 3D-MPL combined with various vehicles strongly enhances both the humoral and a TH1 type of cellular immunity.

QS21: is a natural saponin molecule extracted from the bark of the South American tree *Quillaja saponaria* Molina. A purification technique developed to separate the individual saponines from the crude extracts of the bark, permitted the isolation of the particular saponin, QS21, which is a triterpene glycoside demonstrating stronger adjuvant activity and lower toxicity as compared with the parent component. QS21 has been shown to activate MHC class I restricted CTLs to several subunit Ags, as well as to stimulate Ag specific lymphocytic proliferation (Kensil, 1992). Aquila (formally Cambridge Biotech Corporation) produces and supplies QS21 to SB-Biologicals.

Experiments performed at SmithKline Beecham Biologicals have demonstrated a clear synergistic effect of combinations of MPL and QS21 in the induction of both humoral and TH1 type cellular immune responses.

The oil/water emulsion is composed of an organic phase made of 2 oils (a tocopherol and squalene), and an aqueous phase of PBS containing Tween 80 as emulsifier. The emulsion comprised 5% squalene 5% tocopherol 0.4% Tween 80 and had an average particle size of 180 nm and is known as SB62 (see WO 95/17210).

Experiments performed at SmithKline Beecham Biologicals have proven that the adjunction of this O/W emulsion to 3D-MPL/QS21 (SBAS2) further increases the immunostimulant properties of the latter against various subunit antigens.

2. Preparation of Emulsion SB62 (2 Fold Concentrate):

Tween 80 is dissolved in phosphate buffered saline (PBS) to give a 2% solution in the PBS. To provide 100 ml two fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M110S microfluidics machine. The resulting oil droplets have a size of approximately 180 nm.

3. Preparation of Lipoprot. D1/3-MAGE-3-His QS21/3D MPL Oil in Water (SBS2) Formulation:

The adjuvant is formulated as a combination of MPL and QS21, in an oil/water emulsion. This preparation is delivered in vials of 0.7 ml to be admixed with the lyophilised antigen (vials containing from 30 to 300 μg antigen).

The composition of the adjuvant diluent for the lyophilised vaccine is as follows:

| Ingredients: | Quantity (per dose): |
|---|---|
| Adjuvants | |
| SB62 Emulsion: | 250 µl |
| Squalene | 10.7 mg |
| DL α-tocopherol | 11.9 mg |
| Tween 80 | 4.8 mg |
| Monophosphoryl Lipid A | 100 µg |
| QS21 | 100 µg |
| Preservative | |
| Thiomersal | 25 µg |
| Buffer | |
| Water for injection | q.s. ad 0.5 ml |
| Dibasic sodium phosphate | 575 µg |
| Monobasic potassium phosphate | 100 µg |
| Potassium chloride | 100 µg |
| Sodium chloride | 4.0 mg |

The final vaccine is obtained after reconstitution of the lyophilised LPD-MAGE-3-His preparation with the adjuvant or with PBS alone.

The adjuvants controls without antigen were prepared by replacing the protein by PBS.

4. Vaccine Antigen: Fusion Protein Lipoprotein D1/3-MAGE-3-His:

Lipoprotein D is a lipoprotein exposed on the surface of the Gram-negative bacteria *Haemophilus influenzae*.

The inclusion of the first 109 residues of the processed protein D as fusion partner is incorporated to provide the vaccine antigen with a T-cell epitopes. Besides the LPD moiety, the protein contains two unrelated amino acids (Met and Asp), amino acid residues 3-314 of Mage-3, two Gly residues functioning as hinge region to expose the subsequent seven His residues.

EXAMPLE V

Immunogenicity of LPD-MAGE-3-His in Mice and Monkeys

In order to test the antigenicity and immunogenicity of the human MAGE-3 protein, the candidate vaccine was injected into 2 different mouse strains (C57BL/6 and Balb/C), varying in their genetic background and MHC alleles. For both mouse strains, potential MHC class-I and MHC class-II peptide motifs were theoretically predicted for the MAGE part of the LPD-MAGE-3-His fusion protein.

a)—Immunization Protocol:

5 mice of each strain were injected twice at 2 weeks interval in the foot pad with 5 µg of LPD-MAGE-3-His, formulated or not in SBAS2 at ¹⁄₁₀th of the concentration used in human settings.

b)—Proliferation Assay:

Lymphocytes were prepared by crushing the spleen or the popliteal lymph nodes from the mice, 2 weeks after the last injection. $2\times10^5$ cells were placed in triplicate in 96 well plates and the cells were re-stimulated in vitro for 72 hours with different concentrations (1-0.1 µg/ml) of His-Mage 3 as such or coated onto latex micro-beads.

Figure 5:
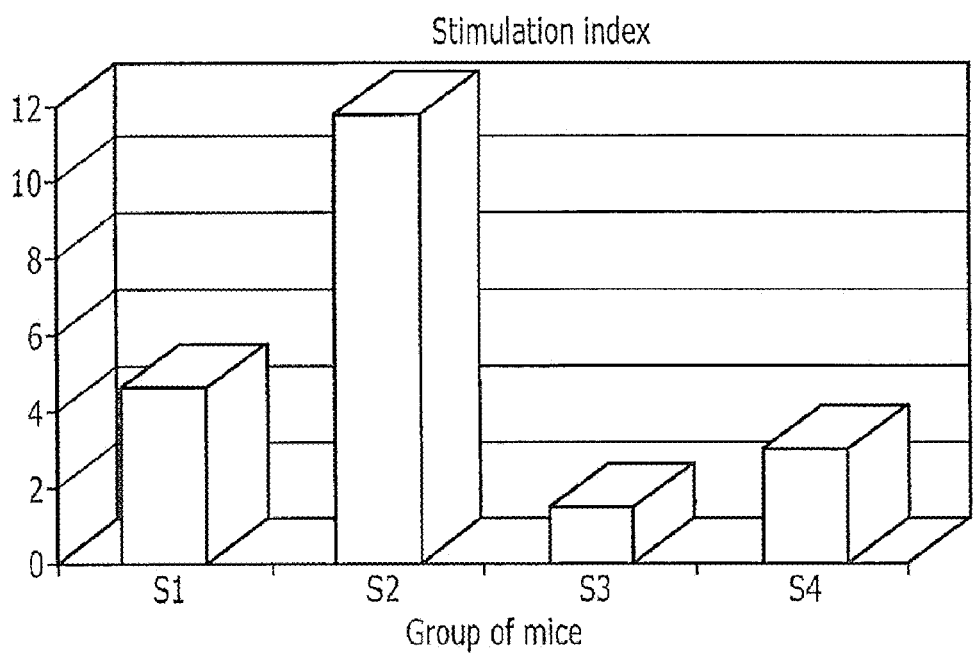

An increased MAGE-3 specific lymphoproliferative activity was observed with both spleen cells (see FIGS. 5 and 7) and lymph node cells (see FIGS. 6 and 8) from either C57BL/6 or Balb/C mice injected with the LPD-MAGE-3-His protein, as compared with the lymphoproliferative response of mice having received the SBAS-2 formulation alone or PBS.

Figure 6:
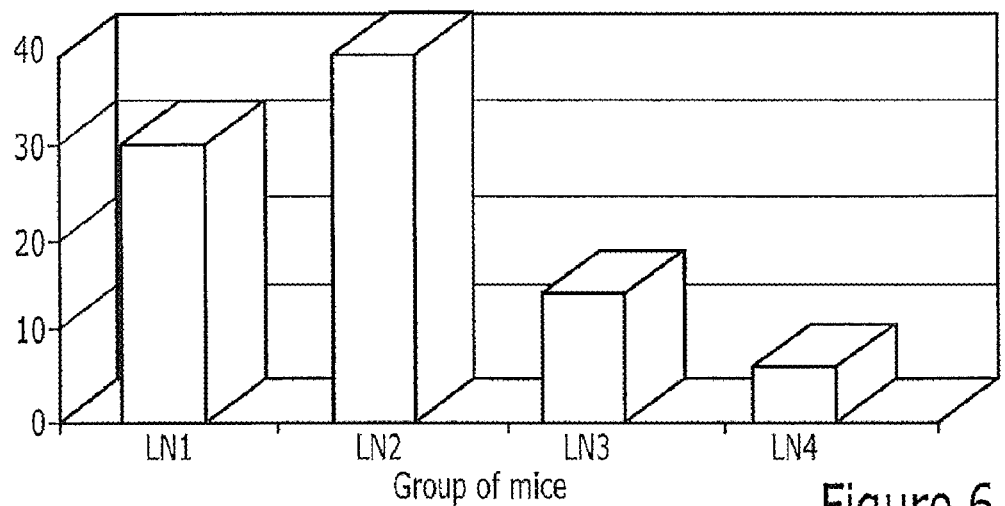
FIG. 6: Immunogenicity of MAGE-3 in mice (C57BL6)
Figure 7A:
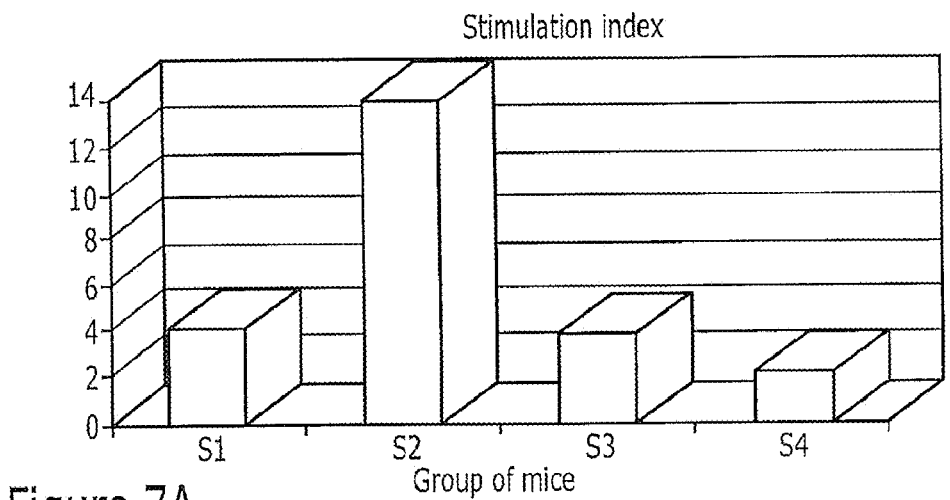
FIG. 7: Immunogenicity of MAGE-3 in mice (BalbC)
Figure 7B:
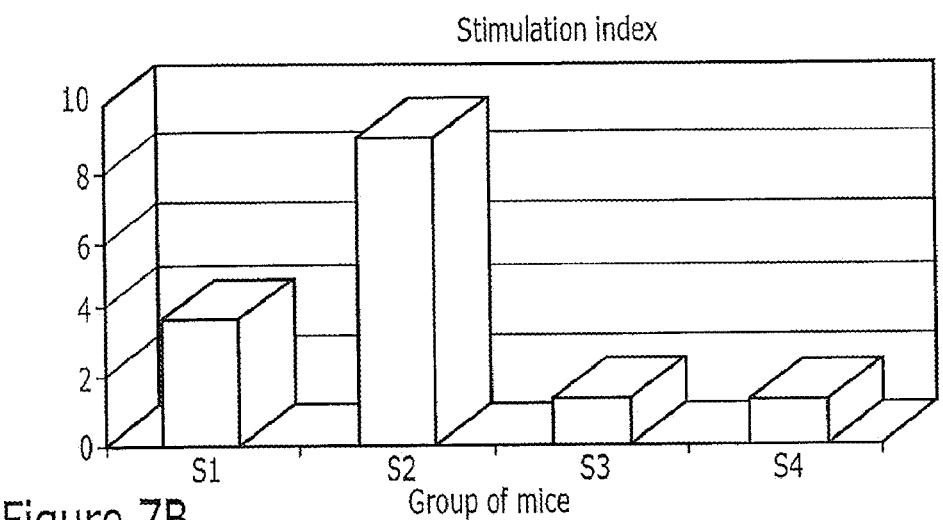
Figure 8A:
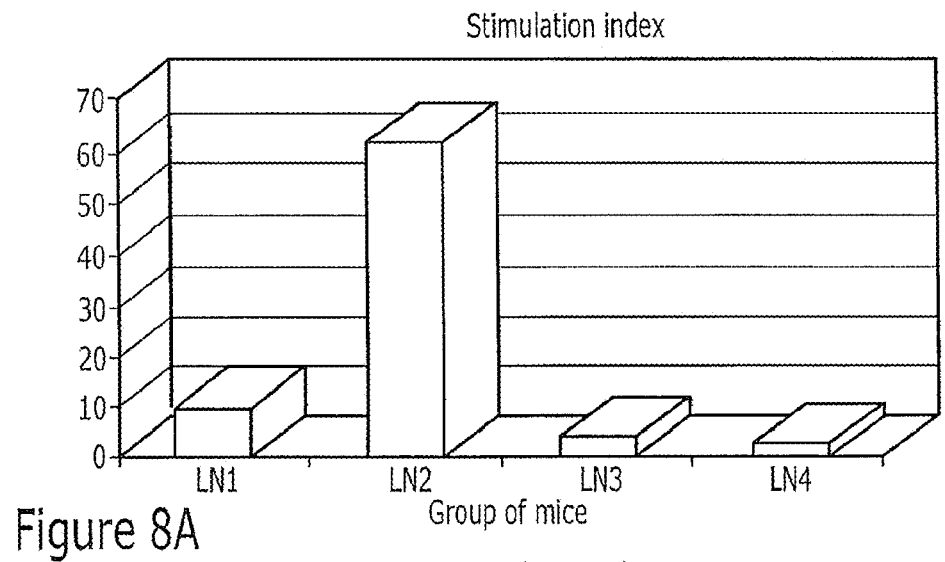
FIG. 8: Immunogenicity of MAGE-3 in mice (BalbC)
Figure 8B:
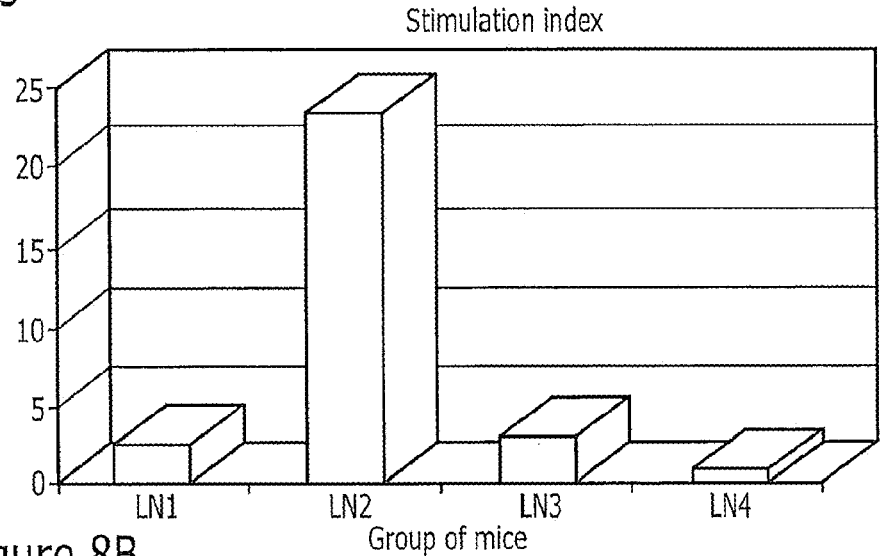

Moreover, a significant higher proliferative response was obtained with lymphocytes from mice immunized with LPD-MAGE-3-His in the adjuvant SBAS2 (see FIGS. 6 and 8).

c)—Conclusion:

LPD-MAGE-3-His is immunogenic in mice, and this immunogenicity can be increased by the use of the SBAS2 adjuvant formulation.

2. Antibody Response:

a)—Immunization Protocol:

Balb/c or C57BL/6 mice were immunized by 2 intra foot pad injections at 2 weeks interval with either PBS, or SBAS2, or 5 µG of LPD-MAGE-3-His, or 5 µG of LPD-MAGE-3-His+SBAS2.

Three and five animals were used in the control groups and in the tested groups respectively.

b)—Indirect ELISA:

Two weeks after the second injection, individual sera were taken and submitted to an indirect ELISA.

Figure 9A:
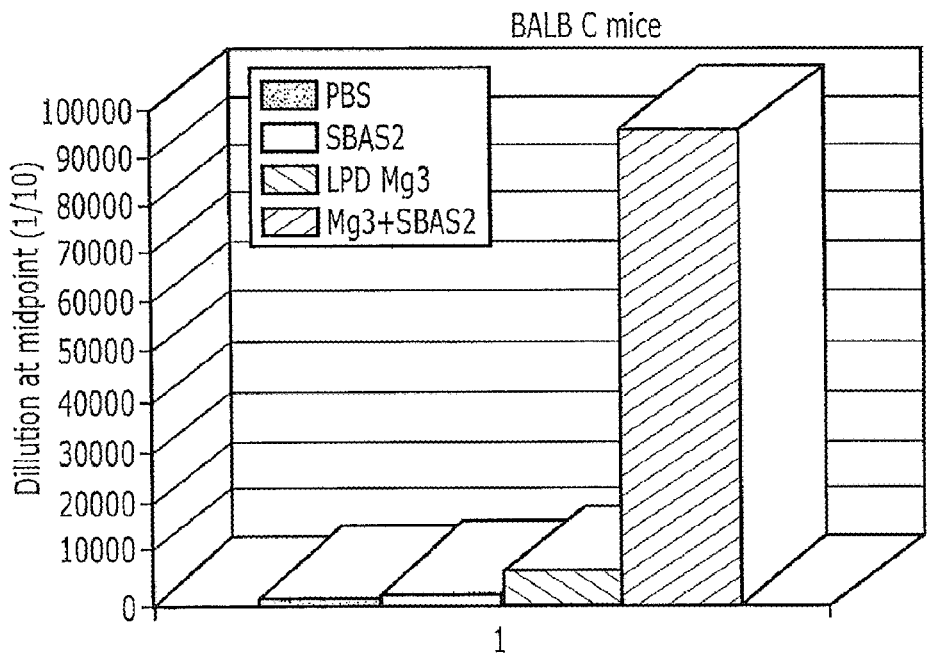
FIG. 9: Anti-Mage antibodies in the serum of mice immunized with LipoD Mage3 His in SBAS2 or not
Figure 9B:
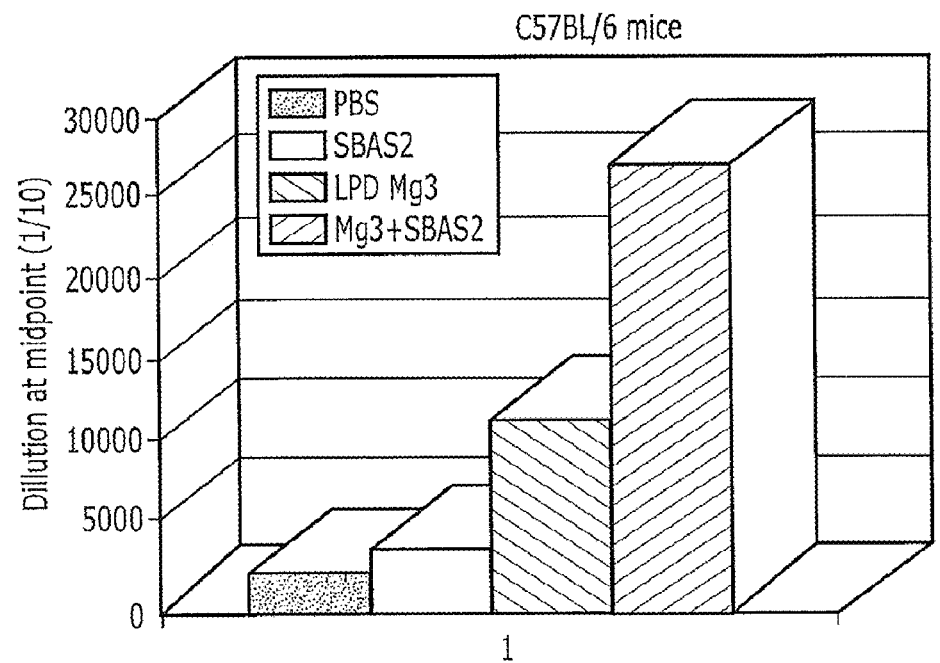
Figure 10A:
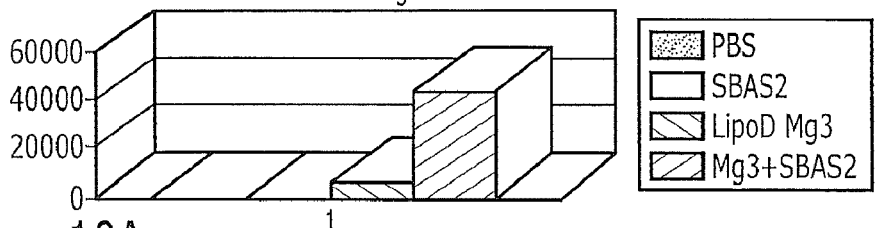
FIG. 10: Subclass-specific antibody responses in Balc/b mice
Figure 10B:
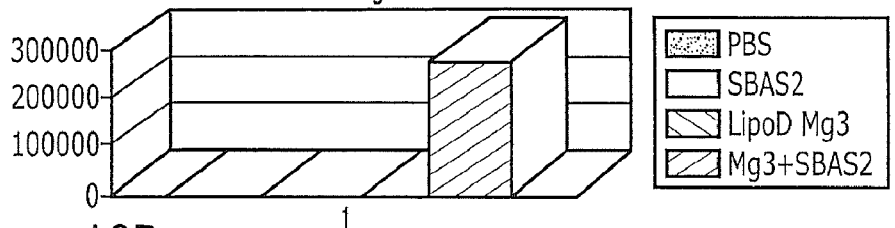
Figure 10C:
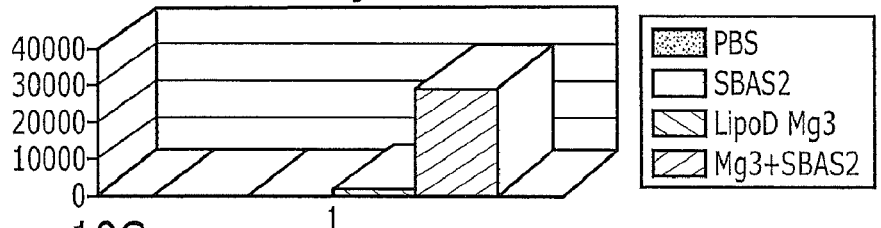
Figure 10D:
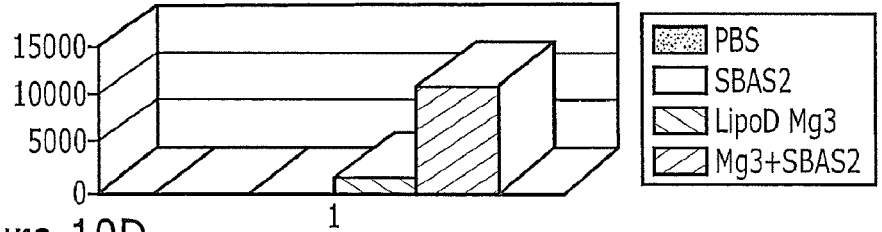
Figure 11A:
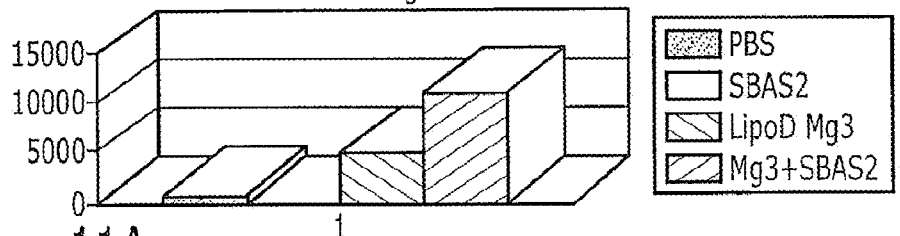
FIG. 11: Subclass-specific antibody responses in C57BL/C mice
Figure 11B:
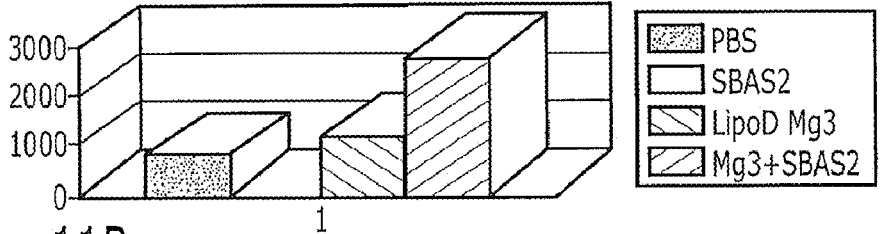
Figure 11C:
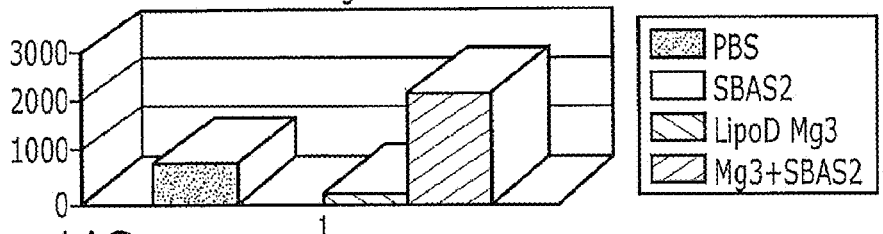
Figure 11D:
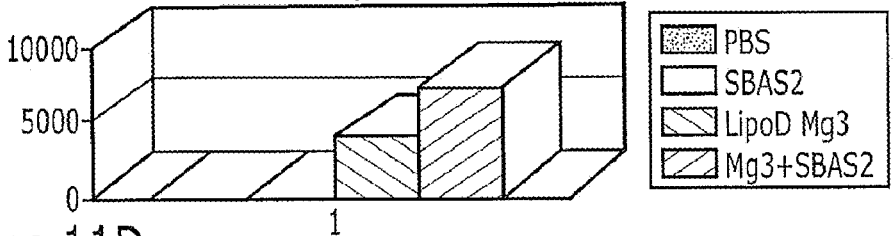

2 µG/ml of purified His MAGE 3 was used as coated antigen. After saturation during 1 hour at 37° C., in PBS+1% newborn calf serum, the sera were serially diluted (starting at 1/1000) in the saturation buffer and incubated overnight at 4° C., or 90 minutes at 37° C. After washing in PBS/Tween 20.01%, Biotinylated goat anti-mouse total IgG (1/1000) or goat anti-mouse IgG1, IgG2a, IgG2b antisera (1/5000) were used as second antibodies. After 90 minutes incubation at 37° C. Streptavidin coupled to peroxidase was added, and TMB (tetra-methyl-benzidine peroxide) was used as substrate. After 10 minutes the reaction was blocked by addition of $H_2SO_4$ 0.5M, and the O.D. was determined c)—Results:

FIG. 9 compares between the different groups of mice (N=5/group), the relative mean midpoint titer of the sera, which consists in the mean dilution needed to reach the midpoint of the curves.

These results show that in both mouse strains tested, a weak Ab response is mounted after 2 injections of LPD-MAGE-3-His alone, but that higher anti-MAGE 3 Ab concentrations are generated when LPD-MAGE-3-His is injected in the presence of SBAS2. Thus, only 2 injections of LPD-MAGE-3-His+SBAS2, at 2 weeks interval, are sufficient to generate the high Ab response observed.

The better Ab response observed in the Balb/c mice as compared with the response obtained in the C57BL/6 mice can be explained by differences in haplotypes or in background between these 2 strains, even though the Ab titre achieved in C57BL/6 mice is also higher after injections of LPD-MAGE-3-His+SBAS2 than after injections with LPD-MAGE-3-His alone.

The Ig subclasses-specific anti-MAGE-3 responses after vaccinations in the different groups of mice can be seen on the FIGS. 10 and 11, which give a comparison of the mean midpoint dilution of the sera.

Neither IgA, nor IgM were detected in any of the serum samples even from the mice vaccinated with LPD-MAGE-3-His in the adjuvant SBAS2.

On the contrary, the total IgG level was slightly higher in the sera from mice vaccinated with LPD-MAGE-3-His alone, and significantly increased in the sera of animals injected with LPD-MAGE-3-His in SBAS2.

The analysis of the different IgG-subclasses concentrations show that a mixed Ab response was induced in the mice, since the levels of all IgG subclasses tested (IgG1, IgG2a, IgG2b) were higher in mice vaccinated with the adjuvanted Ag than in mice injected with the Ag or the adjuvant alone.

The nature of this mixed Ab response after vaccination with LipoD-MAGE 3 in the presence of SBAS2 seems however to depend on the mouse strain, since IgG1 and IgG2b were predominantly found in the sera of Balb/c and C57BL/6 mice respectively.

3. Immunogenicity of Lipoprotein D1/3 MAGE-3-His+ SBAS2 Adjuvant in Rhesus Monkeys Three groups of five Rhesus (Macaca Mulatta) animals were selected. RTS,S and gp120 were used as positive control.

Groups:
Group 1
right leg: RTS,S/SBAS2
left leg: GP120/SBAS2
Group 2
right leg: RTS,S/SB26T
left leg: GP120/SB26T
Group 3
right leg: LipoD1/3 Mage 3 His/SBAS2

The animals received vaccine at day 0 and were boosted at day 28, and 84 and bled to determine their antibody response to both the MAGE 3 and protein D component. The vaccines were administered intramuscularly as a bolus injection (0.5 ml) in the posterior part of the right leg.

Small blood samples were taken every 14 days. Unheparinized blood samples of 3 ml were collected from the femoral vein, were allowed to clot for at least 1 hour and centrifuged at room temperature for 10 minutes at 2500 rpm.

Serum was removed, frozen at −20° C. and sent for determination of the antibody levels by specific Elisa.

96 well microplates (maxisorb Nunc) were either coated with 5 µg of His Mage 3 or Protein D overnight at 4° C. After 1 hour saturation at 37° C. with PBS NCS 1%, serial dilution of the rabbit sera were added for 1 H 30 at 37° C. (starting at 1/10), after 3 washings in PBS Tween, anti rabbit biotinylated serum (Amersham ref RPN 1004 lot 88) was added (1/5000). Plates were washed and peroxydase couple streptavidin (1/5000) was added for 30 minutes at 37° C. After washing, 50 µl TMB (BioRad) was added for 7 minutes and the reaction was stopped with H2S04 0.2M, OD was measured at 450 nm. Midpoint dilutions were calculated by SoftmaxPro.

Antibody Response:

Small blood samples were taken every 14 days to follow the kinetic of the antibody response to Mage 3 by ELISA. The results indicates that after one injection of LPD1/3 Mage 3 His+SBAS2, the Mage 3 specific total Ig titer was low, a clear boost was seen in 3 out of 5 animals after a second and a third injection of LipoD1/3 Mage 3+adjuvant in the same monkeys. The poor responders remained negative even after 3 injections. 28 days post II or post III, the antibody titers has returned to basal levels. The subclass of these antibodies was determined as predominantly IgG and not IgM. The switch to IgG suggests that a T helper response has been triggered. The Protein D specific antibody response, although weaker, is exactly parallel to the Mage 3 antibody response.

EXAMPLE VI

1. LPD-MAGE 1 His

In an analogous fashion—LPD-MAGE 1-His was prepared. The amino acid and DNA sequences are depicted in SEQ ID NO:3 and SEQ ID NO:4. The resulting protein was purified in an analogous manner to the LPD-MAGE-3-His protein. Briefly, the cell culture were homogenized and treated with 4M guanidine HCl and 0.5 M beta mercaptoethanol in the presence of 0.5% Empigen detergent. The product was filtered and the permeate treated with 0.6 M iodoacetamide. The carboxyamidated fractions was subjected to IMAC (zinc Chealate-sepharose FF) chromatography. The column was first equilbrated and washed with a solution containing 4M guanidine. HCl and sodium phosphate (20 mM, pH7.5) and 0.5% Empigen, then the column was washed with a solution containing 4M urea in sodium phosphate (20 mM, pH7.5) 0.5% Empigen buffer. The protein was eluted in the same buffer, but with increasing concentration of Imidazole (20 mM, 400 mM and 500 mM).

The eluate was diluted with 4M Urea. The Q-sepharose column was equilibrated and washed with 4M Urea in 20 mM phosphate buffer (pH7.5) in the presence of 0.5% Empigen. A second wash was performed in the same buffer, but devoid of the detergent. The protein eluted in the same buffer but with increasing Imidazole (150 mM, 400 mM, 1M). The eluate was ultra filtered.

EXAMPLE VII

Figure 12:
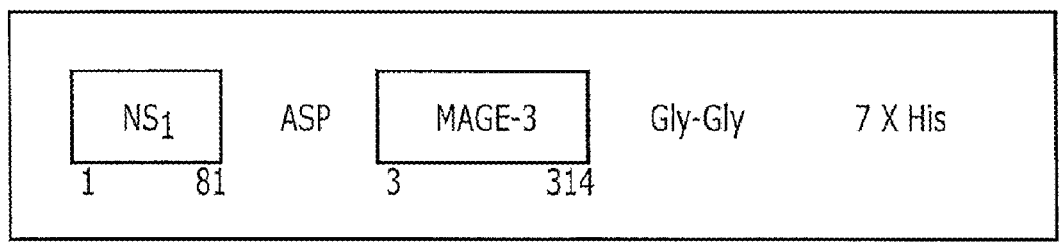
FIG. 12: NS-Asp-MAGE-3-Gly-Gly-7Xhis

Construction of the Expression Plasmid pRIT14426 and Transformation of the Host Strain AR58 to Produce NS1-MAGE-3 His Protein Design:

The design of the fusion protein NS1,-MAGE-3-His to be expressed in E. coli is described in FIG. 12.

The primary structure of the resulting protein has the sequence set forth in SEQ ID No:5.

The coding sequence (SEQ ID No:6) corresponding to the above protein design was placed under the control of λpL promoter in a E. coli expression plasmid.

The Cloning Strategy for the Generation of $NS_1$-MAGE-3-His Fusion Protein:

The starting material was a cDNA plasmid received from Dr Tierry Boon from the Ludwig Institute, containing the coding sequence for MAGE-3 gene and the vector PMG81, containing the 81aa of $NS_1$ (Non structural protein) coding region from Influenza.

Figure 13:
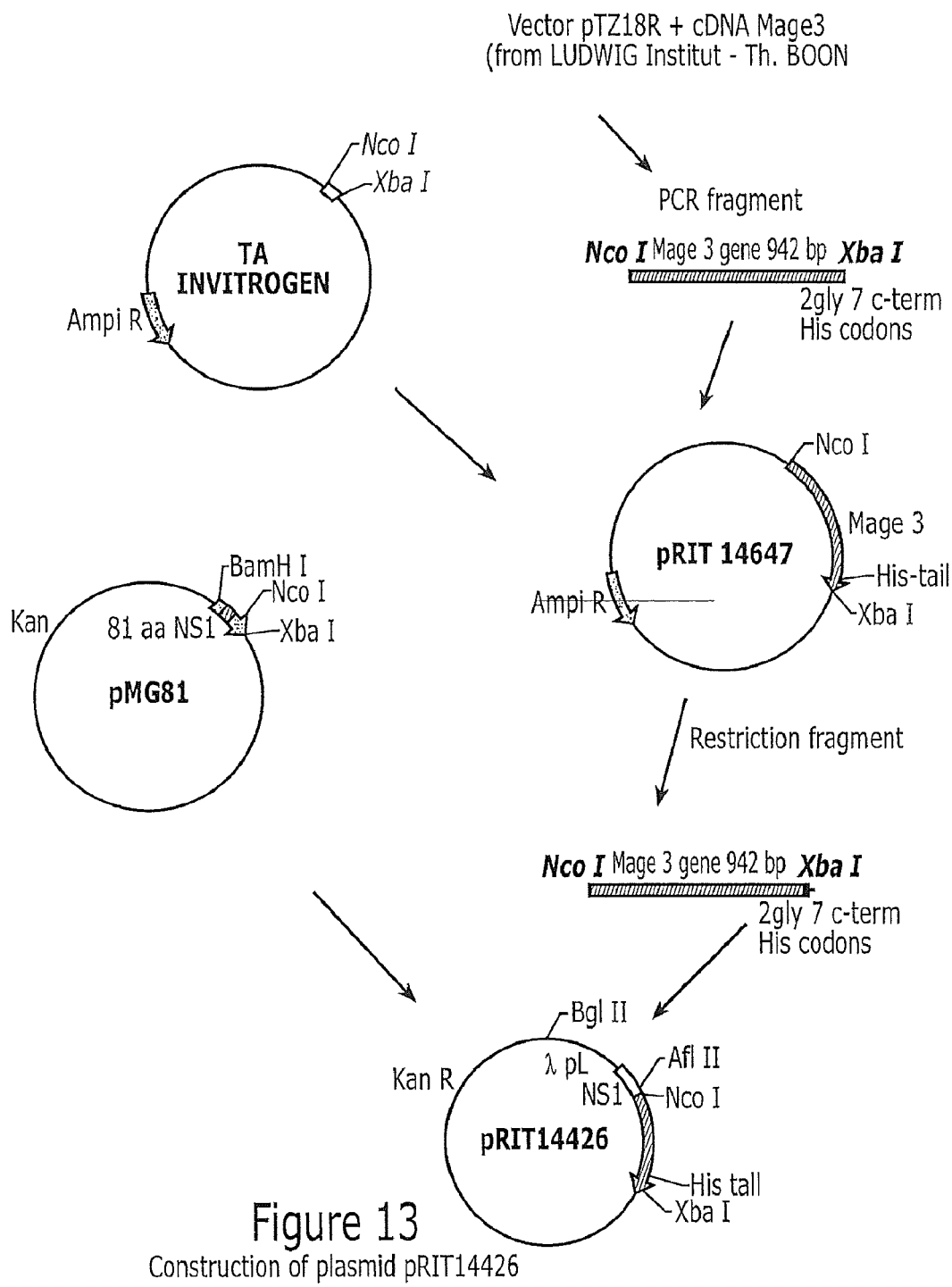
FIG. 13: Construction of plasmid pRIT14426

The cloning strategy outlined in FIG. 13 included the following steps:

a) PCR amplification of the sequences presented in the plasmid cDNA MAGE-3 using the oligonucleotide sense: 5' gc gcc atg gat ctg gaa cag cgt agt cag cac tgc aag cct (SEQ ID NO:11), and the oligonucleotide antisense: 5' gcg tct aga tta atg gtg atg gtg atg gtg atg acc gcc ctc ttc ccc ctc tct caa (SEQ ID NO:12).

Figure 14:
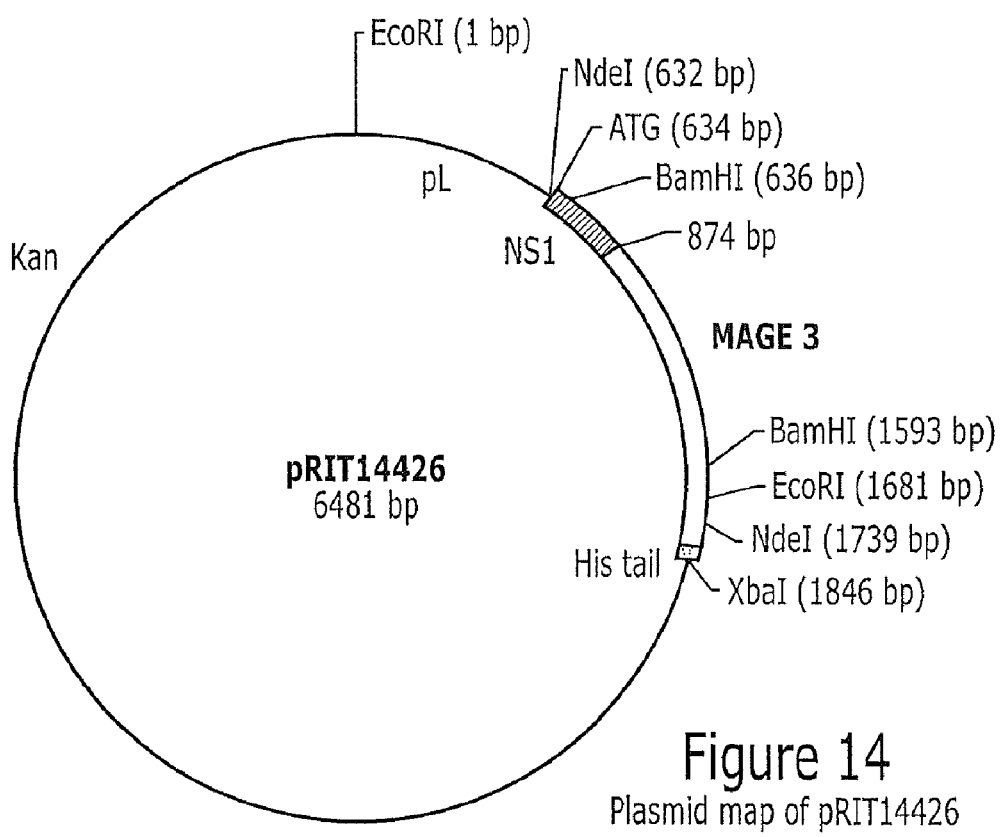
FIG. 14: Plasmid map of pRIT14426

This amplification leads to the following modifications at the N terminus: changing of the first five codons to the E. coli codon usage, replacement of the Pro codon by an Asp codon at position 1, installation of an NcoI site at the 5' extremity and finally addition of the 2 Gly codons and the 7 His codon followed by an XbaI site at the C-terminus.

b) Cloning into the TA cloning vector of invitrogen of the above amplified fragment and preparation of the intermediate vector pRIT14647 c) Excision of the NcoI XbaI fragment form plasmid pRIT14647 and cloning into the vector pRIT PMG81 d) Transformation of the host strain AR58 e) Selection and characterization of the E. coli strain transformants containing the plasmid pRIT14426 (see FIG. 14) expressing the NS1-MAGE-3-His fusion protein Characterization of the Recombinant $NS_1$-MAGE-3-His (pRIT14426):

Bacteria were grown on LB Medium supplemented with 50 μg/ml kanamycin at 30° C. When the culture had reached OD=0.3 (at 620 nm), heat induction was achieved by raising the temperature to 42° C.

After 4 hours induction, cells were harvested, resuspended in PBS and lysed (by disintegration) by pressing three times in the French press. After centrifugation (60 minutes at 100,000 g), pellet supernatant and total extract were analyzed by SDS-PAGE. Proteins were visualized in Coomassie B1 stained gels where the fusion protein represented about 1% of the total *E. coli* proteins. The recombinant protein appeared as a single band with an apparent MW of 44,9 K. The fusion protein was identified by Western Blot analysis using anti-NS 1 monoclonal.

EXAMPLE VIII

Purification of NS1-MAGE 3-His (*E. Coli*) for Rabbit/Mice Immunization.

Purification Scheme:

The following purification scheme was used to purify the antigen:

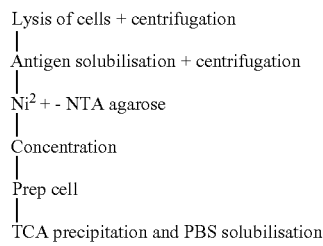

a. Lysis

Bacterial cells (23 g) were lysed in 203 ml of a 50 mM PO$_4$ pH7 buffer by Rannie (homogeniser) and the lysate was centrifuged in a JA 20 rotor at 15,000 rpm during 30 minutes.

The supernatant was discarded.

b. Antigen Solubilisation

⅓ of the pellet was resolubilised O/N at 4° C. in 34 ml of 100 mM PO$_4$—6 M GuHCl pH7. After centrifugation in a JA 20 rotor at 15,000 rpm for 30 minutes, the pellet was discarded and the supernatant was further purified by IMAC.

c. Affinity Chromatography: Ni$^2$+-NTA Agarose (Qiagen)

Column volume: 15 ml (16 mm×7.5 cm)

Packing buffer: 0.1 M PO$_4$—6 M GuHCl pH7

Sample buffer: idem

Washing buffer: 0.1 M PO$_4$—6 M GuHCl pH7

0.1M PO$_4$—6 M urea pH7

Elution: imidazol gradient (0→250 mM) in 0.1 M PO$_4$ buffer pH7 supplemented with 6 M urea.

Flow rate: 2 ml/min a. Concentration:

Antigen positive fractions of the IMAC eluate (160 ml) were pooled and concentrated to 5 ml in an Amicon stirred cell on a Filtron membrane (type Omega cut-off 10,000). The purity at this stage is about 70% as estimated by SDS-PAGE.

b. Preparative Electrophoresis (Prep Cell Biorad)

2.4 ml of the concentrated sample was boiled in 0.8 ml reducing sample buffer and loaded on a 10% acrylamide gel. The antigen was eluted in a Tris-Glycine buffer pH 8.3 supplemented with 4% SDS and Ns$_1$-MAGE 3 His positive fractions were pooled.

a. TCA Precipitation:

The antigen was TCA precipitated and after centrifugation in a JA 20 rotor at 15,000 rpm for 20 minutes, the supernatant was discarded. The pellet was resolubilised in PBS buffer pH 7.4.

The protein is soluble in PBS after freeze/thaw does not show any degradation when stored for 3 hours at 37° C. and has an apparent molecular weight of approximately 50,000 Daltons as determined by SDS (12.5% PAGE).

EXAMPLE IX

Figure 15:
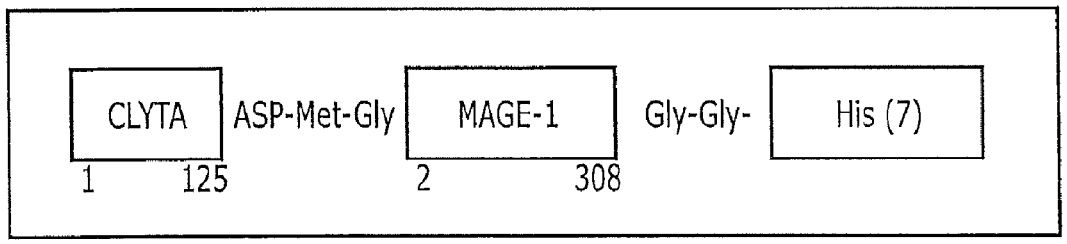
FIG. 15: CLYTA-Asp-Met-Gly-MAGE-1-Gly-Gly-His(7)

Preparation of the *E. coli* Strain Expressing a Fusion Protein CLYTA-MAGE-1-His Tail 1. Construction of the Expression Plasmid pRIT14613 and Transformation of the Host Strain AR58:

Protein Design:

The design of the fusion protein Clyta-Mage-1-His to be expressed in *E. coli* is described in FIG. 15.

The primary structure of the resulting protein has the sequence set forth in SEQ ID No:7.

The coding sequence (see SEQ ID No:8) corresponding to the above protein design was placed under the control of λ pL promoter in a *E. coli* expression plasmid.

Cloning:

The starting material was the vector PCUZ1 that contains the 117 C-terminal codons of the LytA coding region from *Streptococcus pneumoniae* and the vector pRIT14518, in which we have previously subcloned the MAGE-1 gene cDNA from a plasmid received from Dr Thierry Boon from the Ludwig Institute.

Figure 16:
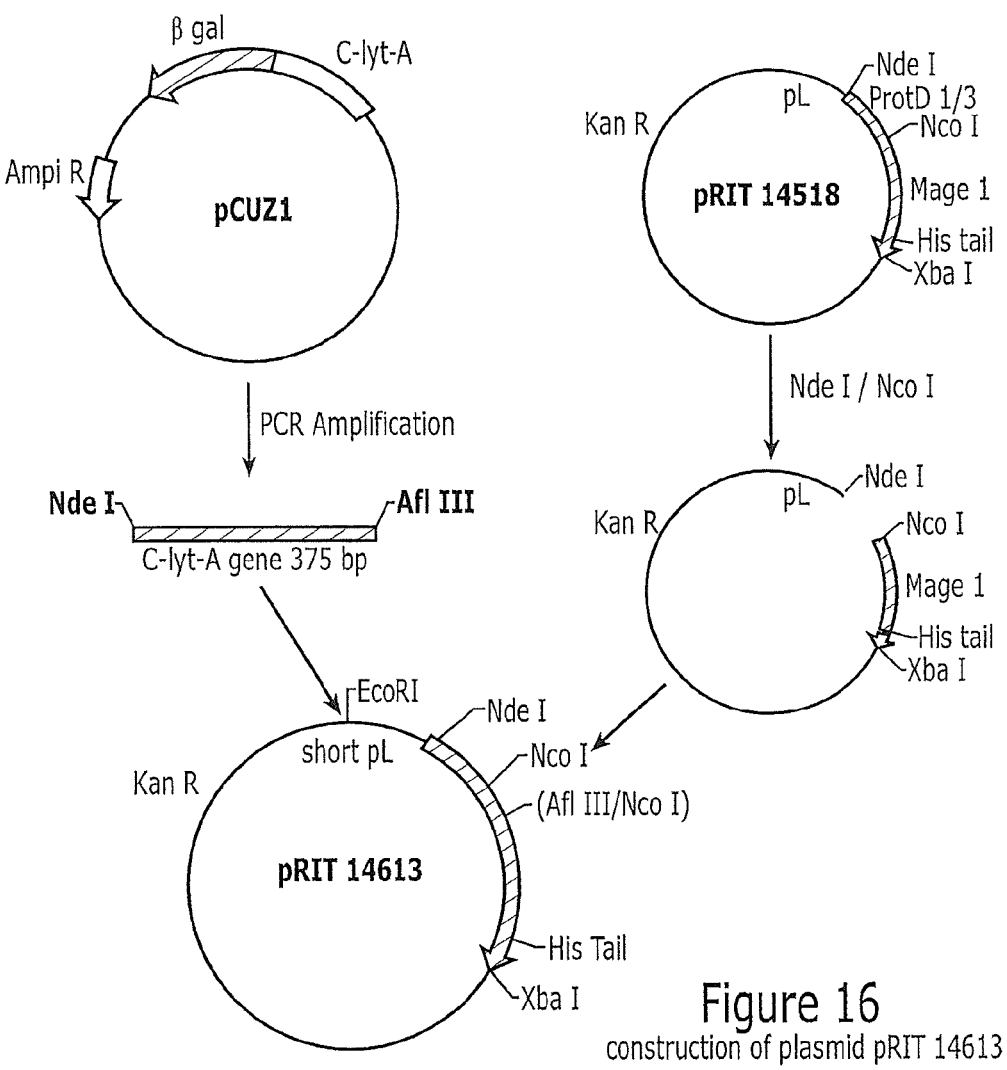
FIG. 16: Construction of plasmid pRIT14613

The cloning strategy for the expression of CLYTA-Mage-1-His protein (see outline in FIG. 16) included the following steps:

2. Preparation of the CLYTA-Mage-1-his Coding Sequence Module:

a) The first step was a PCR amplification, destined to flank the CLYTA sequences with the NdeI-AflIII restriction sites. The PCR amplification was done using the plasmid PCUZ1 as template and as primers the oligonucleotide sense: 5' tta aac cac acc tta agg agg ata taa cat atg aaa ggg gga att gta cat tca gac (SEQ ID NO:13), and the oligonucleotide antisense: 5' GCC AGA CAT GTC CAA TTC TGG CCT GTC TGC CAG (SEQ ID NO:14). This leads to the amplification of a 378 nucleotides long CLYTA sequence.

b) The second step was linking of CLYTA sequences to the MAGE-1-His sequences, to generate the coding sequence for the fusion protein. This step included the excision of a NdeI-AflIII Clyta fragment and insertion into the vector pRIT14518 previously opened by NdeI and NcoI (NcoI and AflIII compatible) restriction enzymes and gave rise to the plasmid pRIT14613.

c) Transformation of the host strain AR58 d) Selection and characterization of the *E. coli* transformant (KAN resistant) containing the plasmid pRIT14613. (See FIG. 16)

1. Characterization of the Recombinant Protein CLYTA-MAGE-1-His (pRIT14613):

Bacteria were grown on LB Medium supplemented with 50 μg/ml kanamycin at 30° C. When the culture had reached OD=0.3 (at 620 nm), heat induction was achieved by raising the temperature to 38° C.

After 4 hours induction, cells were harvested, resuspended in PBS and lysed (by disintegration) by one shot. After centrifugation, pellet supernatant and total extract were analyzed by SDS-PAGE. Proteins were visualized in Coomassie B1 stained gels, where the fusion protein represented about 1% of the total *E. coli* proteins. The recombinant protein appeared as a single band with an apparent MW of about 49 kD. The fusion protein was identified by Western Blot analysis using anti-Mage-1 polyclonal antibodies.

Reconstitution of the Expression Unit Composed by the Long λ pL Promoter (Useful for Nalidixic Acid Induction) and the CLYTA-Mage-1 Coding Sequence pRIT14614):

A EcoRI-NCO$_1$ restriction fragment containing the long PL promoter and a part of CLYTA sequences was prepared from plasmid pRIT DVA6 and inserted between the EcoRI-NCO$_1$ sites of plasmid pRIT14613.

The recombinant plasmid pRIT14614 was obtained.

Figure 17:
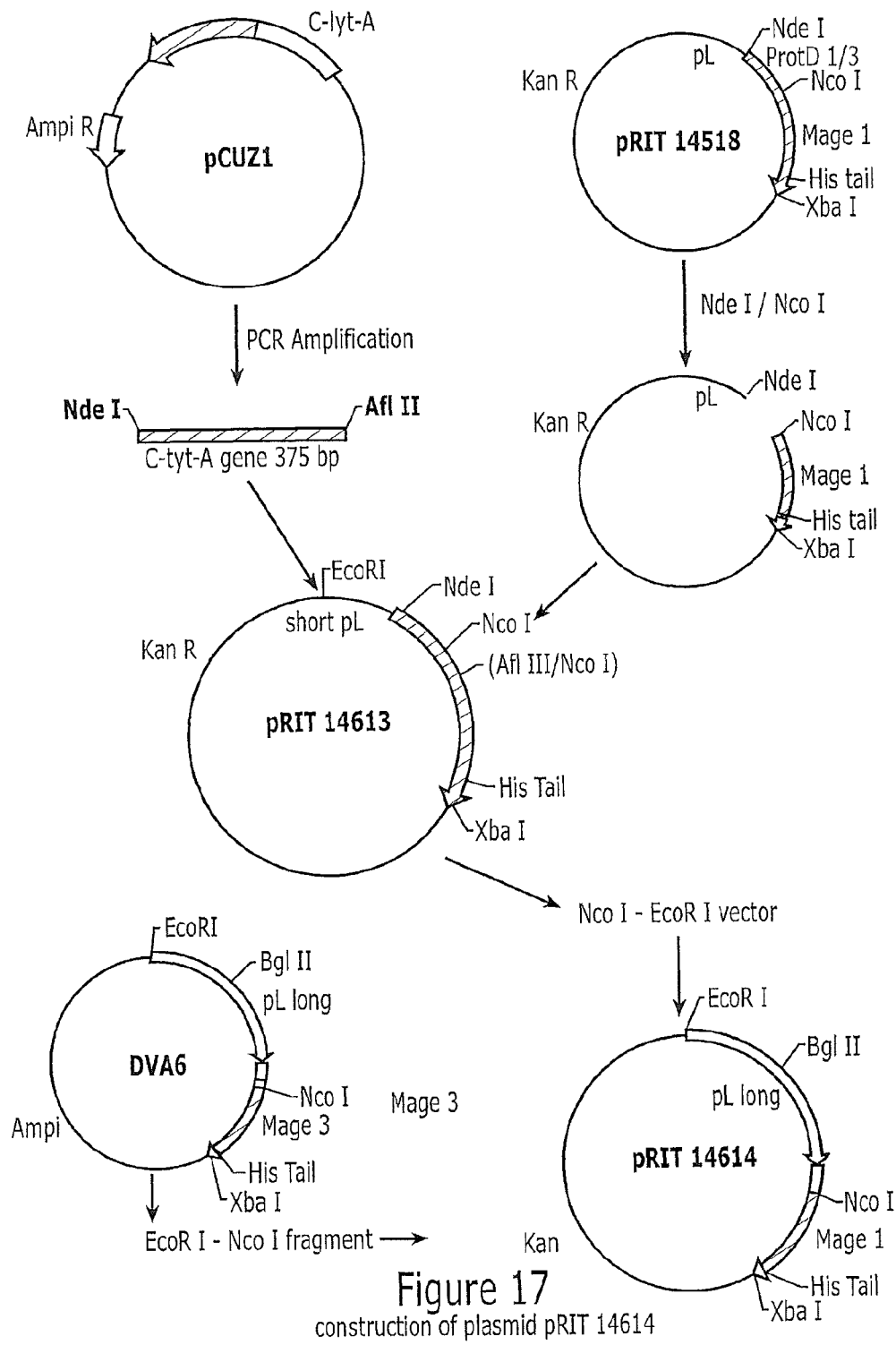
FIG. 17: Construction of plasmid pRIT

The recombinant plasmid pRIT14614 (see FIG. 17) encoding the fusion protein CLYTA-Mage-1-His was used to transform *E. coli* AR120. A Kan resistant candidate strain was selected and characterized.

Characterization of the Recombinant Protein:

Bacteria were grown on LB Medium supplemented with 50 mg/ml kanamycin at 30° C. When the culture had reached OD=400 (at 620 nm) Nalidixic acid was added to a final concentration of 60 mg/ml.

After 4 hours induction, cells were harvested, resuspended in PBS and lysed by desintegration (disintegration CLS "one shot" type). After centrifugation, pellet supernatant and total extract were analyzed by SDS-PAGE. Proteins were visualized in Coomassie Bleu stained gels, where the fusion protein represented about 1% of the total *E. coli* proteins. The fusion protein was identified by Western blot analysis using rabbits anti-Mage-1 polyclonal antibodies. The recombinant protein appeared as a single band with an apparent MW of about 49 kD.

EXAMPLE X

CLYTA-MAGE-3-HIS

A: Tumour rejection recombinant antigen: a fusion protein CLYTA-Mage-3-His where the C-lyt A fusion partner lead to expression of a soluble protein, act as affinity tag and provides a useful T-helper.

Figure 18:
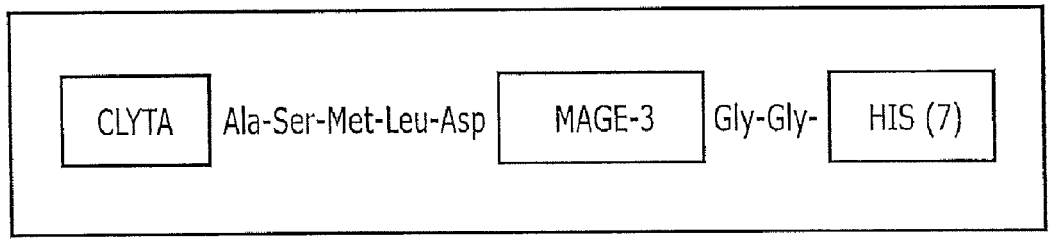
FIG. 18: CLYTA-Asp-Ser-Met-Leu-Asp-MAGE-3-Gly-Gly-His(7)

Preparation of the *E. coli* strain expressing a fusion protein CLYTA-Mage-3-His tail Construction of the expression plasmid pRIT14646 and transformation of the host strain AR 120:

Protein Design:

The design of the fusion protein Clyta-Mage-3-His to be expressed in *E. coli* is described in FIG. 18.

The primary structure of the resulting protein has the sequence described in SEQ ID No:9 and the coding sequence in SEQ ID No:10.

The coding sequence corresponding to the above protein design was placed under the control of λ pL promoter in a *E. coli* expression plasmid.

Cloning:

The starting material was the vector PCUZ1 that contains the 117 C-terminal codons of the LytA coding region from *Streptococcus pneumoniae*, described in Gene 43, (1986) p. 265-272 and the vector pRIT14426, in which we have previously subcloned the MAGE-3 gene cDNA from a plasmid received from Dr Tierry Boon from the Ludwig Institute.

Figure 19:
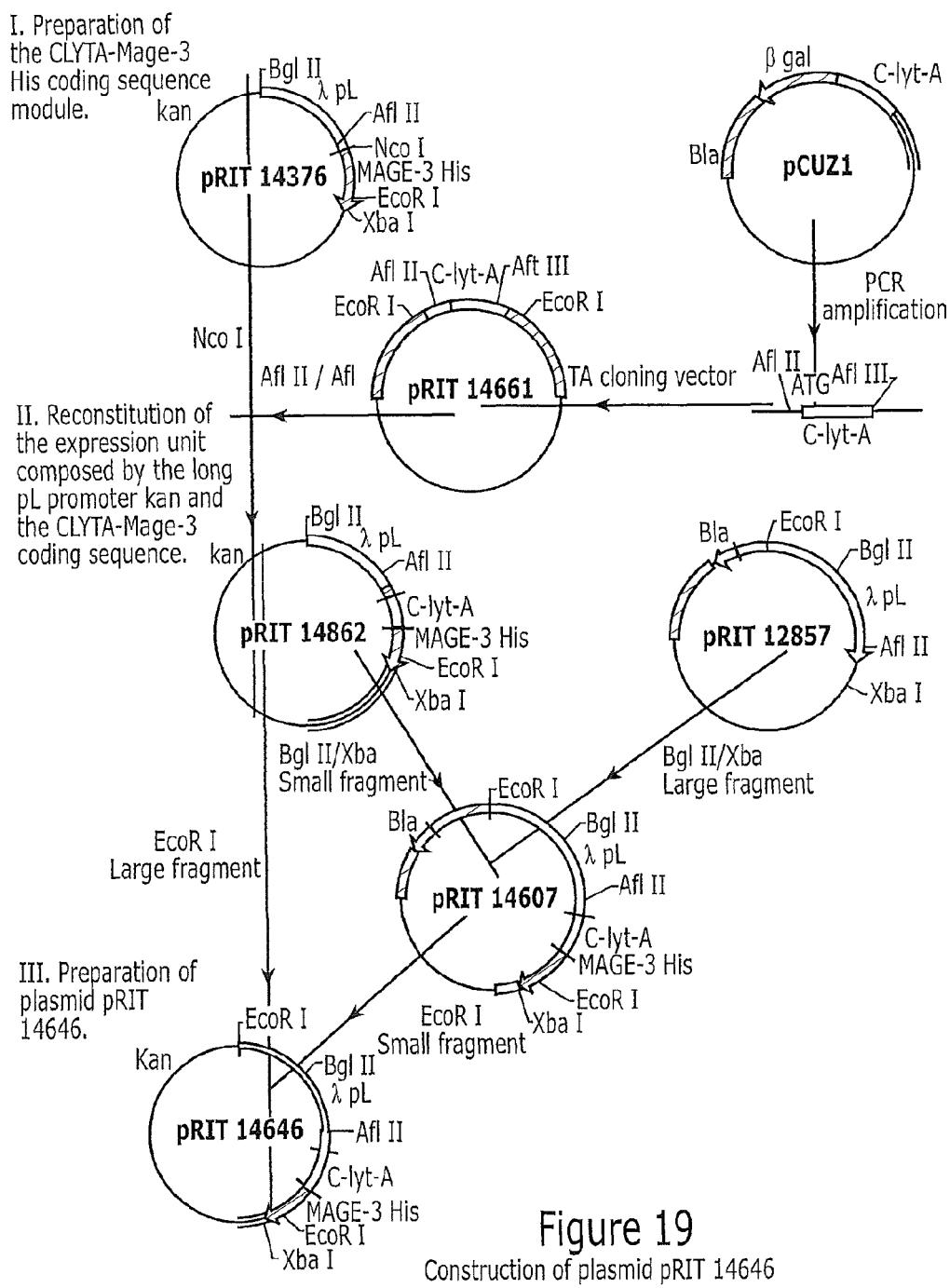
FIG. 19: Construction of plasmid pRIT 14646

The cloning strategy for the expression of CLYTA-MAGE-3-His protein (see outline in FIG. 19) included the following steps:

1—Preparation of the CLYTA-MAGE-3-His Coding Sequence Module:

1.1 The first step was a PCR amplification, destined to flank the CLYTA sequences with the AflII and AflIII restriction sites. The PCR amplification was done using the plasmid PCUZ1 as template and as primers the oligonucleotide sense: 5' tta aac cac acc tta agg agg ata taa cat atg aaa ggg gga att gta cat tca gac (SEQ ID NO:13), and the oligonucleotide antisense: 5' ccc aca tgt cca gac tgc tgg cca att ctg gcc tgt ctg cca gtg (SEQ ID NO:15). This leads to the amplification of a 427 nucleotides long CLYTA sequence. The above amplified fragment was cloned into the TA cloning vector of Invitrogen to get the intermediate vector pRIT14661

1.2 The second step was linking of CLYTA sequences to the MAGE-3-His sequences, to generate the coding sequence for the fusion protein. This step included the excision of a AflII-AflIII Clyta fragment and insertion into the vector pRIT14426 previously opened by Afl II and NcoI (NcoI and AflII compatible) restriction enzymes and gave rise to the plasmid pRIT14662.

2.—Reconstitution of the Expression Unit Composed by the Long λ pL Promoter (Useful for Nalidixic Acid Induction) and the CLYTA-Mage-3 Coding Sequence:

A BglII-XbaI restriction fragment containing the short pL promoter and the CLYTA-Mage-3-His coding sequences was prepared from plasmid pRIT14662. and inserted between the BglII-XbaI sites of plasmid TCM67 (a pBR322 derivative containing the resistance to ampicillin, and the long λ pL promoter, described in the international application PCT/EP92/01827). The plasmid pRIT14607 was obtained.

The recombinant plasmid pRIT14607 encoding the fusion protein Clyta-Mage-3 His was used to transform *E. coli* AR 120 (Mott et a1.1985, Proc. Natl. Acad. Sci, 82: 88). An ampicillin resistant candidate strain was selected and characterized.

3. Preparation of Plasmid pRIT 14646:

Finally a plasmid similar to pRIT 14607 but having the Kanamycin selection was constructed (pRIT 14646)

Characterization of the Recombinant Protein:

Bacteria were grown on LB Medium supplemented with 50 mg/ml kanamycin at 30° C. When the culture had reached OD=400 (at 600 nm) Nalidixic acid was added to a final concentration of 60 ?g/ml.

After 4 hours induction, cells were harvested, resuspended in PBS and lysed by desintegration (desintegration CLS "one shot" type). After centrifugation, pellet supernatant and total extract were analyzed by SDS-PAGE. Proteins were visualized in Coomassie Bleu stained gels, where the fusion protein represented about 1% of the total *E. coli* proteins. The fusion protein was identified by Western blot analysis using rabbits anti-Mage-3 polyclonal antibodies. The recombinant protein appeared as a single band with an apparent MW of about 58 kD.

EXAMPLE XI

Purification of the Recombinant Protein CLYTA-Mage-3 His

The recombinant bacteria AR120 (pRIT 14646) were grown in a 20 Litters fermentor under fed-batch conditions at 30°. The expression of the recombinant protein was induced by adding Nalidixic acid at a final concentration of 60 ?g/ml. Cells were harvested at the end of fermentationand and lyzed at 60OD/600 by two passages through a French Press disrupter (20 000 psi). Lysed cells were pelleted 20 min at 15 000 g at 4° C. Supernatant containing the recombinant protein was loaded onto exchange DEAE Sepharose CL6B resin (Pharmacia) pre-equilibrated in 0.3M NaCl, 20 mM Tris HCl pH 7.6 Buffer A. After a column wash with buffer A, fusion protein was eluted by 2% choline in (Buffer A). Positive antigen fractions, as revealed by Western blotting analysis using an anti Mage-3 antibody, were pooled. DEAE-eluted antigen was brought to 0.5% Empigen BB (a zwitterionic detergent) and to 0.5 M NaCl before loading onto an Ion Metal Affinity chromatography column preequilibrated in 0.5% Empigen BB, 0.5 M NaCl, 50 mM phosphate buffer pH 7.6 (Buffer B).

IMAC column was washed with buffer B until 280 nm absorbency reached the base line. A second wash in buffer B without Empigen BB (Buffer C) in order to eliminate the detergent was executed before Antigen elution by an Imidazole gradient 0-250 mM Imidazole in buffer C.

0.090-0.250 M Imidazole fractions were pooled, concentrated on a 10 kDa Filtron omega membrane before dialysis versus PBS buffer.

CONCLUSION

We have demonstrated that the fused protein LPD-MAGE3-His is immunogenic in mice, and that this immunogenicity (the proliferative response and antibody response) can be further increased by the use of the adjuvant described above. Purification can be enhanced by derivatising the thiols that form disulphide bonds.

We have also demonstrated that a better antibody response was triggered by the vaccination with the LPD-MAGE-3-His in the presence of the adjuvant. The predominant isotype found in the serum of C57BL/6 being IgG2b suggesting that a TH1 type immune response was raised.

In the human, clinical setting a patient treated with LPD-MAGE3-His in an unadjuvanted formulation was cleared of melanoma.

REFERENCES

Anichini A., Fossati G., Parmiani G. *Immunol. Today,* 8: 385 (1987).

De Plaen E., Arden K., Traversari C., et al. *Immunogenetics,* 40: 360 (1994).

Gaugler B., Van den Eynde B., van der Bruggen P., et al. *J. Exp. Med.,* 179: 921 (1994).

Herman J., van der Bruggen P., Immanuel F., et al. *Immunogenetics,* 43: 377 (1996).

Inoue H., Mori M., Li J., et al. *Int. J. Cancer,* 63: 523 (1995).

Kensil C. R., Soltysik S., Patel U., et al. in: Channock R. M., Ginsburg H. S., Brown F., et al., (eds.), *Vaccines* 92, (Cold Spring Harbor Laboratory Press, Cold Spring Harbor, N.Y.), 36-40: (1992).

Knuth A., Danowski B., Oettgen H. F., et al. *Proc. Natl. Acad. Sci. USA,* 81: 3511 (1984).

Patard J. J., Brasseur F., Gil-Diez S., et al. *Int. J. Cancer,* 64: 60 (1995).

Ribi E., et al. in: Levine L., Bonventre P. F., Morello J., et al. (eds)., American Society for Microbiology, Washington D.C., *Microbiology* 1986, 9-13; (1986).

Van den Eynde B., Hainaut P., Hérin M. et al. *Int. J. Cancer,* 44: 634 (1989).

Van der Bruggen P., Traversari C., Chomez P., et al. *Science,* 254: 1643 (1991).

Van der Bruggen P., Bastin J., Gajewski T., et al. *Eur. J. Immunol.,* 24: 3038 (1994).

Van Pel A., van der Bruggen P., Coulie P. G., et al., *Immunol. Rev.,* 145: 229 (1995).

Weynants P., Lethe B., Brasseur F., et al. *Int. J. Cancer,* 56: 826 (1994).

Nishimura S, Fujita M, Terata N, Tani T, Kodama M, Itoh K, Nihon Rinsho Meneki Gakkai Kaishi 1997, Apr., 20 (2): 95-101.

Fuijie T et al, Ann Oncol 1997 Apr., 8 (4): 369-72.

---

The invention claimed is:

1. A process for the production of an immunogenic polypeptide comprising the steps of:
   (i) treating a polypeptide consisting of SEQ ID NO:2 to reduce a disulfide bond and produce a free thiol group;
   (ii) blocking said free thiol group with a blocking agent;
   (iii) purifying a polypeptide resulting from step (ii) using one or more chromatographic purification steps,
   where the purified polypeptide is immunogenic and contains said blocking agent.

2. The process of claim 1, wherein said blocking agent is iodoacetamide.

3. The process of claim 1, wherein the purified polypeptide is carboxyamidated.

4. The process of claim 1, wherein the purified polypeptide is carboxymethylated.

5. The process of claim 1, wherein the purified polypeptide is lipidated.

6. The process of claim 1, further comprising formulating the purified polypeptide as a pharmaceutical composition.

7. A process for the production of an immunogenic composition comprising the steps of:
   (i) treating a polypeptide consisting of SEQ ID NO:2 to reduce a disulfide bond and produce a free thiol group;
   (ii) blocking said free thiol group with a blocking agent;
   (iii) purifying a polypeptide resulting from step (ii) using one or more chromatographic purification steps, where the purified polypeptide is immunogenic and contains said blocking agent; and
   (iv) formulating the purified polypeptide as a pharmaceutical composition.

8. The process of claim 7, wherein said blocking agent is iodoacetamide.

9. The process of claim 7, wherein the purified polypeptide is carboxyamidated.

10. The process of claim 7, wherein the purified polypeptide is carboxymethylated.

11. The process of claim 7, wherein the purified polypeptide is lipidated.

12. The process of claim 6, where said pharmaceutical composition comprises a pharmaceutically acceptable excipient.

* * * * *